(12) United States Patent
Zhang et al.

(10) Patent No.: US 11,181,526 B2
(45) Date of Patent: Nov. 23, 2021

(54) PEPTIDE, FLUORESCENT PROBE COMPRISING THE SAME, AND PREPARATION METHOD THEREOF

(71) Applicant: Singulprobe Nanjing Biotechnology Co., Ltd, Nanjing (CN)

(72) Inventors: Yuhui Zhang, Wuhan (CN); Yubing Han, Wuhan (CN)

(73) Assignee: SINGULPROBE NANJING BIOTECHNOLOGY CO., LTD, Nanjing (CN)

( * ) Notice: Subject to any disclaimer, the term of this patent is extended or adjusted under 35 U.S.C. 154(b) by 343 days.

(21) Appl. No.: 16/386,311

(22) Filed: Apr. 17, 2019

(65) Prior Publication Data
US 2019/0293657 A1 Sep. 26, 2019

Related U.S. Application Data

(63) Continuation-in-part of application No. PCT/CN2018/084718, filed on Apr. 27, 2018.

(30) Foreign Application Priority Data

Apr. 28, 2017 (CN) .......................... 201710291378.5

(51) Int. Cl.
G01N 33/58 (2006.01)
C07K 7/08 (2006.01)
C07K 14/00 (2006.01)
C09K 11/06 (2006.01)
G01N 21/64 (2006.01)
G01N 33/533 (2006.01)
C07K 7/06 (2006.01)
C07K 5/11 (2006.01)

(52) U.S. Cl.
CPC ......... *G01N 33/582* (2013.01); *C07K 5/1019* (2013.01); *C07K 7/06* (2013.01); *C07K 7/08* (2013.01); *C07K 14/001* (2013.01); *C09K 11/06* (2013.01); *G01N 21/6428* (2013.01); *G01N 21/6486* (2013.01); *G01N 33/533* (2013.01); *C07K 2319/00* (2013.01); *C07K 2319/10* (2013.01); *C09K 2211/10* (2013.01); *G01N 2021/6439* (2013.01)

(58) Field of Classification Search
None
See application file for complete search history.

*Primary Examiner* — Anand U Desai
(74) *Attorney, Agent, or Firm* — Matthias Scholl P.C.; Matthias Scholl

(57) ABSTRACT

A peptide, including: a first peptide fragment including $(KG)_n$ or $(GK)_n$ where n is an integer between 2 and 5, K represents a lysine residue, and G represents a glycine residue; a second peptide fragment including an identification sequence; and a first connection peptide including 1-2 glycine residues. The first connection peptide is disposed between the first peptide fragment and the second peptide fragment.

20 Claims, 18 Drawing Sheets

Specification includes a Sequence Listing.

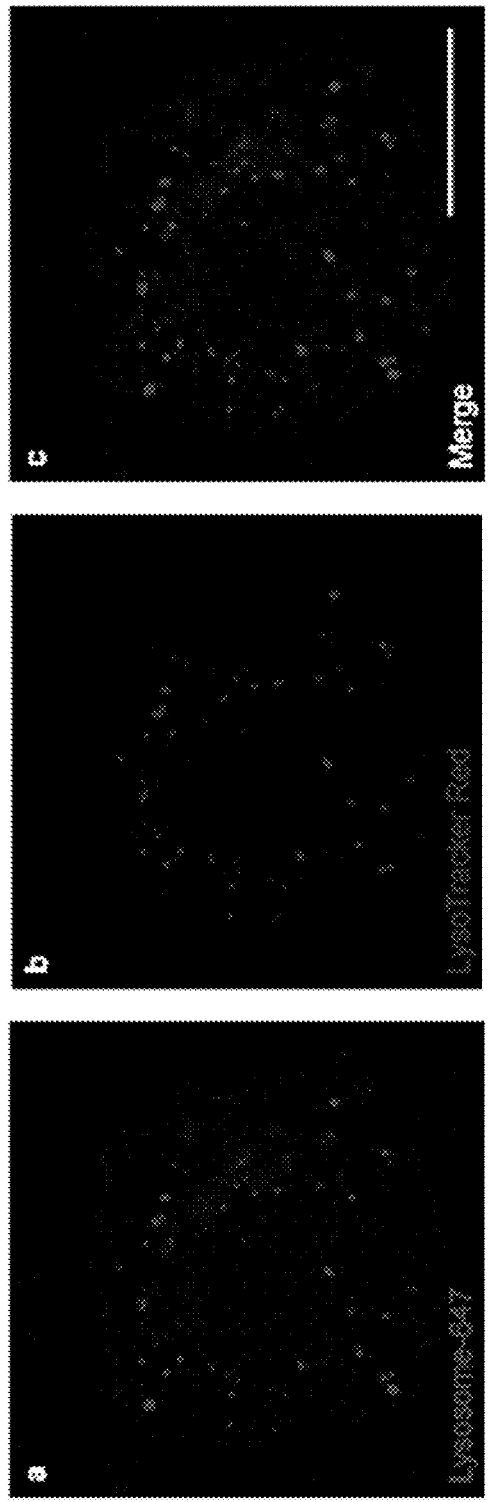

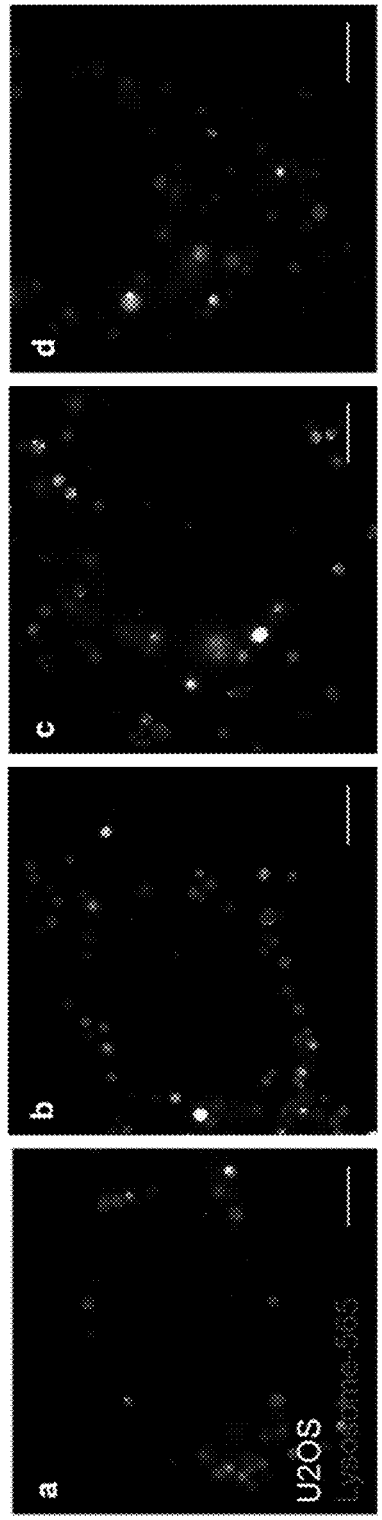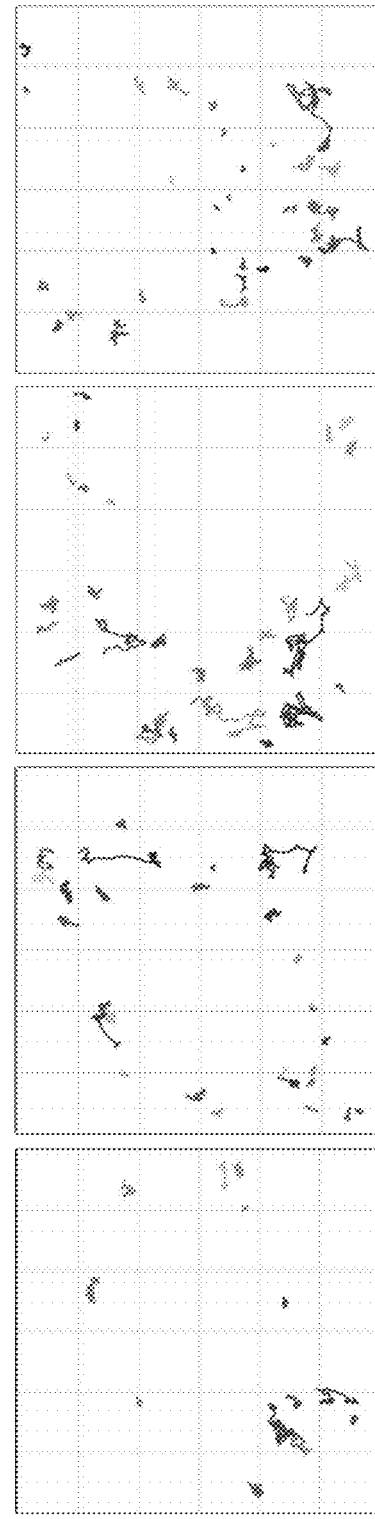
FIG. 6A  FIG. 6B  FIG. 6C  FIG. 6D
FIG. 6E  FIG. 6F  FIG. 6G  FIG. 6H

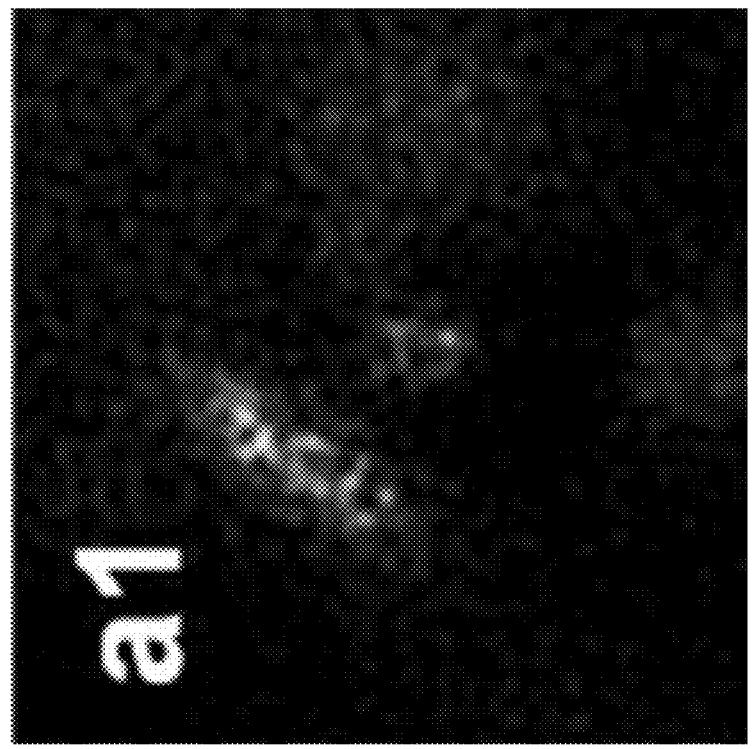
FIG. 8A1
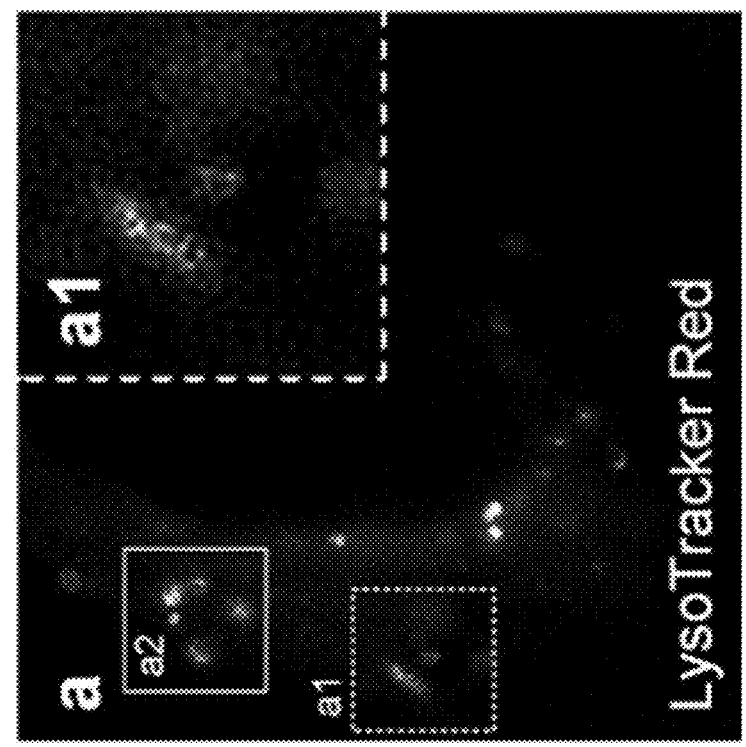
FIG. 8A

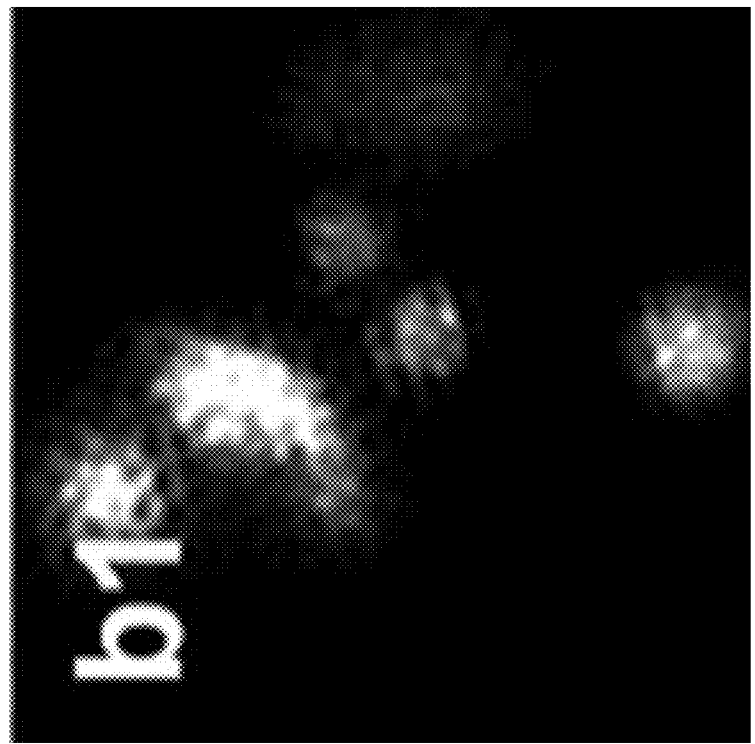
FIG. 8B1
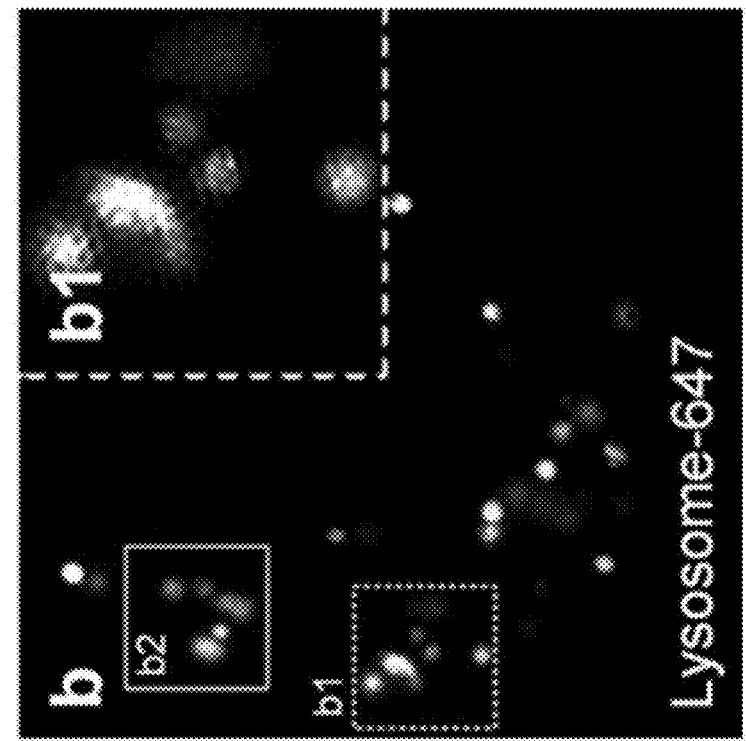
FIG. 8B

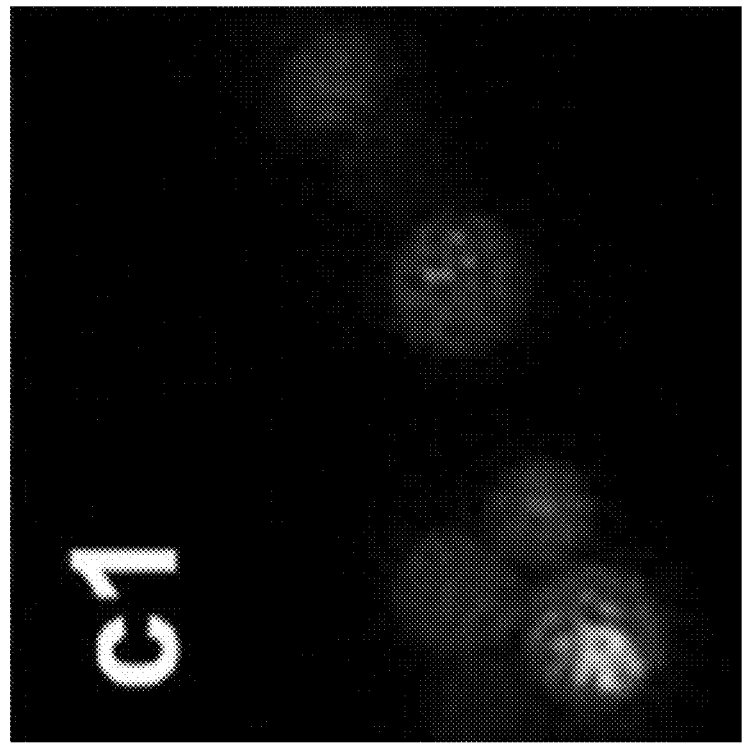
FIG. 8C1
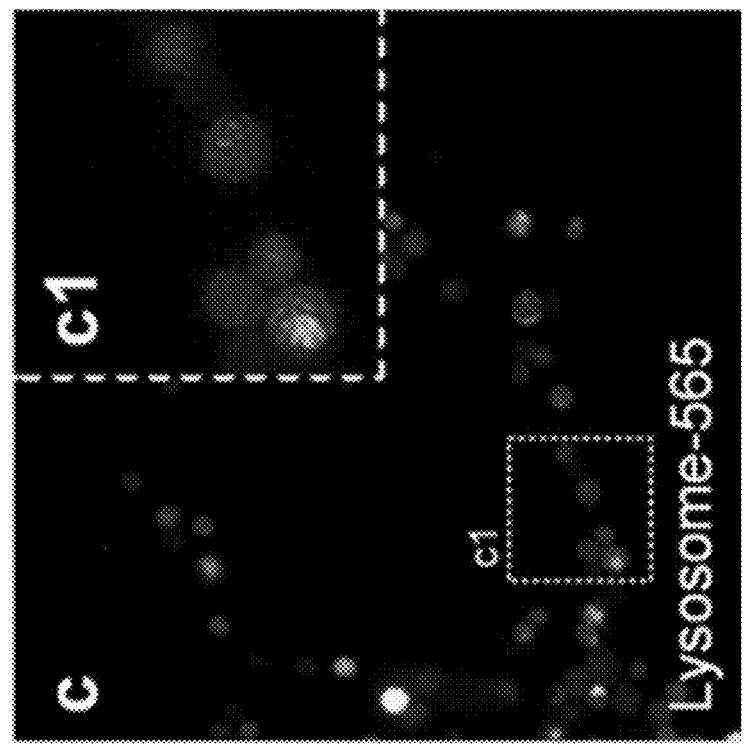
FIG. 8C

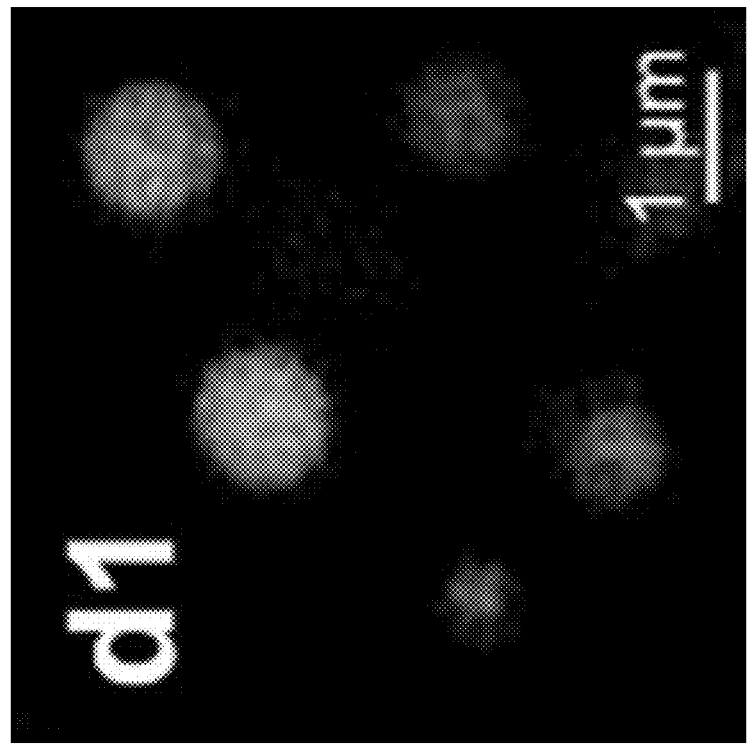
FIG. 8D1
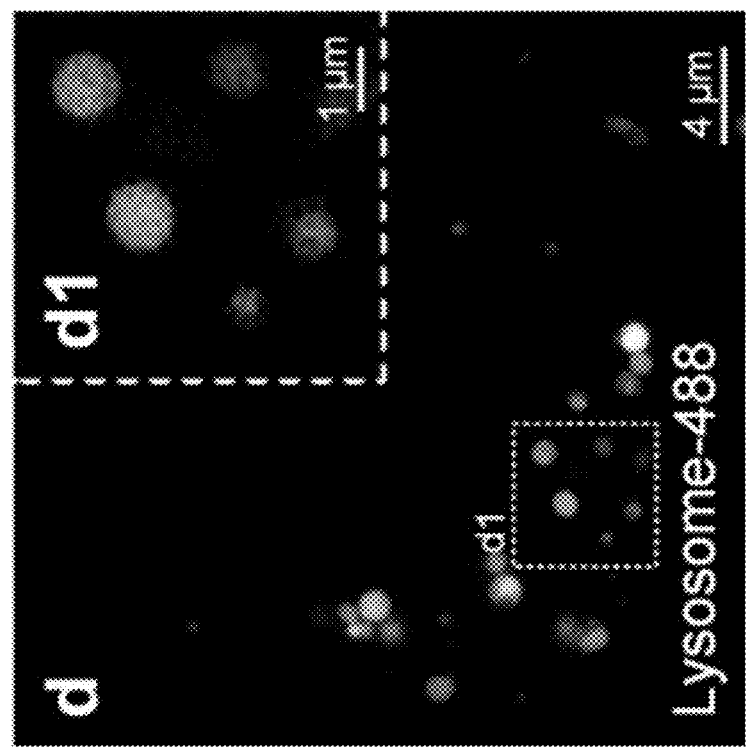
FIG. 8D

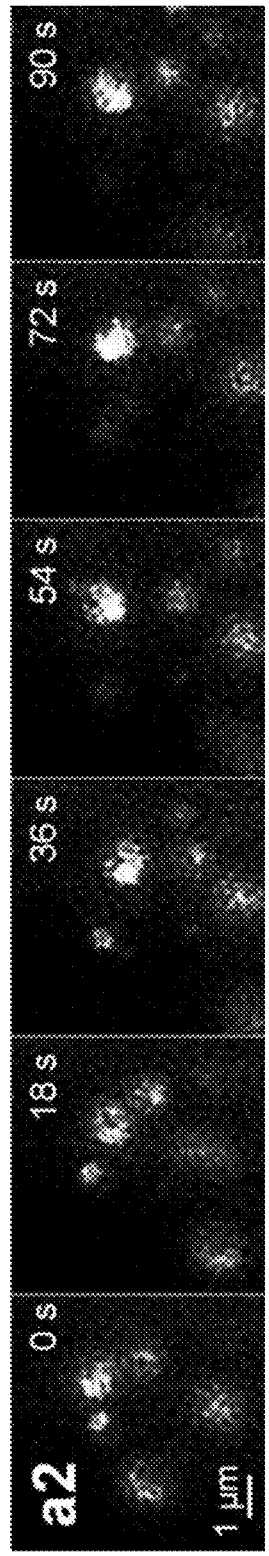
FIG. 8A2
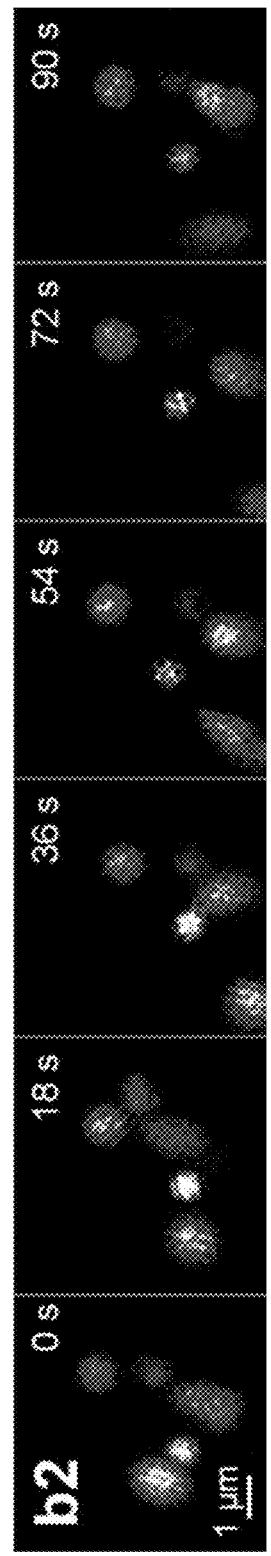
FIG. 8B2

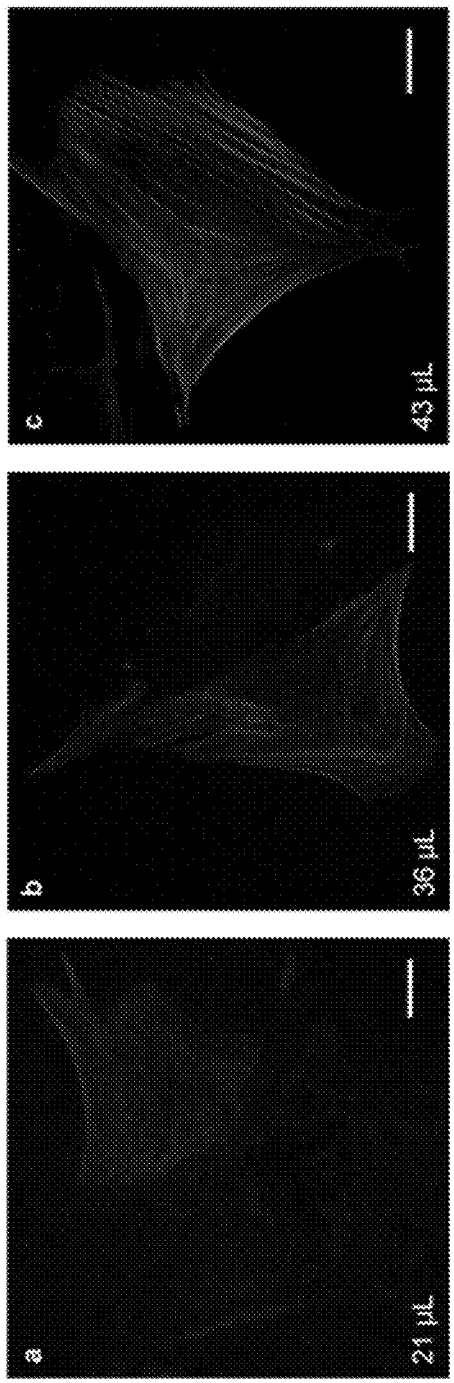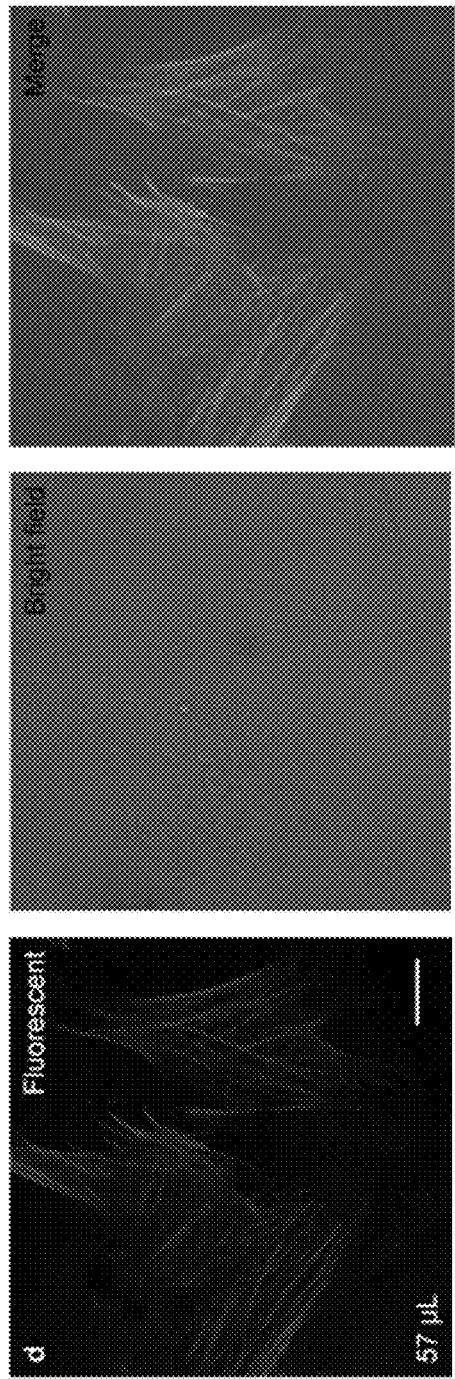
FIG. 9A  FIG. 9B  FIG. 9C  FIG. 9D  FIG. 9E  FIG. 9F

PEPTIDE, FLUORESCENT PROBE COMPRISING THE SAME, AND PREPARATION METHOD THEREOF

CROSS-REFERENCE TO RELATED APPLICATIONS

This application is a continuation-in-part of International Patent Application No. PCT/CN2018/084718 with an international filing date of Apr. 27, 2018, designating the United States, now pending, and further claims foreign priority benefits to Chinese Patent Application No. 201710291378.5 filed Apr. 28, 2017. The contents of all of the aforementioned applications, including any intervening amendments thereto, are incorporated herein by reference.

BACKGROUND

The disclosure relates to a peptide, a fluorescent probe comprising the same, and preparation method thereof.

Conventional fluorescence living-cell labeling methods include:

a) Using a fluorescent protein to label a target protein. The quantum yield of the fluorescent protein is relatively low, thus reducing the imaging resolution and the image quality.

b) Introducing fluorescence-modified macromolecules into living cells through an electroporation method or a microinjection method. The labeling method is costly and involves complex operations.

c) Employing a chemical fluorescent probe to label a target. However, the chemical fluorescent probe may be nonspecific or cell-impermeable.

SUMMARY

This disclosure provides a peptide, a fluorescent probe comprising the peptide and preparation method thereof. The fluorescent probe can be freely coupled to a fluorescent dye and exhibits excellent fluorescent characteristics.

According to one aspect of the disclosure, provided is a peptide, comprising: a first peptide fragment comprising $(KG)_n$ or $(GK)_n$ where n is an integer between 2 and 5, K represents a lysine residue, and G represents a glycine residue; a second peptide fragment comprising an identification sequence; and a first connection peptide comprising 1-2 glycine residues and being disposed between the first peptide fragment and the second peptide fragment.

In $(KG)_n$ or $(GK)_n$, n can be 3.

The peptide can further comprise a cell-permeable peptide fragment connected to the first peptide fragment or the second peptide fragment via a second connection peptide.

The cell-permeable peptide fragment can have the sequence of rRrRrRRR (SEQ ID NO: 1), where R represents D-arginine, and r represents L-arginine.

The second connection peptide can comprise one or two glycine residues.

The second peptide fragment can comprise a recognition unit to cysteine protease C1 or actin.

The disclosure also provides a fluorescent probe comprising the peptide, and the lysine residue of the peptide is coupled to a fluorescent dye.

The fluorescent dye comprises an N-hydroxysuccinimide (NHS) active group.

The fluorescent dye can be selected from Alexa Fluor 647 NHS ester, Cy3B NHS ester, Atto 565 NHS ester and/or Atto 488 NHS ester.

Further provided is a method of preparing the fluorescent probe. The method comprises:

1) synthesizing the peptide by using solid phase synthesis, the peptide being coupled to a resin;
2) separating the peptide from the resin, removing a protective group of a side chain of the peptide, and purifying and concentrating the peptide; and
3) covalently connecting free amino groups of the lysine residue of the peptide obtained in 2) to an NHS active group of the fluorescent dye by using liquid phase reaction to obtain the fluorescent probe.

The method can further comprise: 4) dissolving the fluorescent probe obtained in 3) and purifying the fluorescent probe with reversed-phase chromatography.

Advantages of the embodiments of the disclosure include:

(1) The fluorescent probe is a combination of a peptide fragment and a fluorescent dye, and the amount of the fluorescent dye needed is relatively low. This reduces the cost of the probe, and the selection of the fluorescent dye is flexible.

(2) The peptide is compatible to various fluorescent dyes. The fluorescent probe formed by the peptide and the fluorescent dyes exhibits excellent optical performance, ensuring that a super-resolution image can be generated with high quality.

(3) The fluorescent probe comprises a modularized recognition unit and cell-permeable peptide fragment, which is conducive to a precise positioning of a subcellular structure in living cells, such as actin fiber or a lysosome in a living cell.

(4) The fluorescent probe can be prepared in a modularization manner. A semi-finished probe can be prefabricated and then combined with different fluorescent dyes. Therefore, a variety of probes can be prepared.

BRIEF DESCRIPTION OF THE DRAWINGS

in FIG. 3B, the mother liquor of the probe is 29 µL; in FIG. 3C, the mother liquor of the probe is 43 µL; in FIG. 3D, the mother liquor of the probe is 57 µL; in FIG. 3E, the mother liquor of the probe is 71 µL; FIG. 3F shows a bright-field channel in the labeling state of 71 µL of the mother liquor.

FIGS. 4A-4C show labeling of lysosome by Alexa Fluor 647-based fluorescent probes and standard lysosome marker LysoTracker Red in living cells, where, FIG. 4A shows labeling of a lysosome by Alexa Fluor 647-based fluorescent probes, FIG. 4B shows labeling of a lysosome by LysoTracker Red, and FIG. 4C shows a co-localization image of the previous two labelings.

FIG. 5A shows total internal reflection overlapping imaging prior to calculation at the left bottom, and a super-resolution image of stochastic optical reconstruction after calculation at the lower right angle, and FIG. 5B shows a profile cross-section graph of a lysosome in the white block in FIG. 5A;

FIGS. 6A-6H show super-resolution imaging by structural illumination microscopy of cysteine protease C1 fluorescent probe based on Atto 565, where, FIGS. 6A-6D show a first frame of images of 101 lysosomes in four U2OS cells, and FIGS. 6E-6H show track charts of corresponding lysosomes on a focal plane.

FIGS. 8A-8B2 show super-resolution imaging by structural illumination microscopy of cysteine protease C1 fluorescent probes based on Alexa 647, Atto 565 and Atto 488 and a standard lysosome marker LysoTracker Red, where, FIG. 8A shows imaging of LysoTracker Red, FIG. 8B shows imaging of cysteine protease C1 fluorescent probe based on Alexa 647, FIG. 8C shows imaging of cysteine protease C1 fluorescent probe based on Atto 565, FIG. 8D shows imaging of cysteine protease C1 fluorescent probe based on Atto 488. FIGS. 8A1, 8B1, 8C1 and 8D1 are enlarged views of dotted line blocks in FIGS. 8A, 8B, 8C and 8D respectively, and FIGS. 8A2 and 8B2 are enlarged time-lapsed images of solid line blocks in FIG. 8A and FIG. 8B respectively.

FIGS. 9A-9F show labeling of a lysosome by Alexa Fluor 647-based actin fluorescent probes with different concentrations, where the total volume is 100 μL, in FIG. 9A, the mother liquor of the probe is 21 μL; in FIG. 9B, the mother liquor of the probe is 36 μL; in FIG. 9C, the mother liquor of the probe is 43 μL; in FIG. 9D, the mother liquor of the probe is 57 μL; FIG. 9E shows a bright-field channel in the labeling state of 57 μL of the mother liquor; and FIG. 9F shows a colocalization image of fluorescent channel and bright-field channel labeled by working solution containing 57 μL of probe mother liquor.

FIG. 4A shows labeling of actin by GFP-actin, FIG. 4B shows labeling of actin by Alexa Fluor 647, and FIG. 4C shows a colocalization image of the previous two labelings.

FIGS. 11A-11C show total internal reflection overlapping images of Alexa Fluor 647, Cy3B and Atto488 prior to calculation at the left bottom, respectively, and super-resolution images of stochastic optical reconstruction after calculation at the lower right, respectively; FIGS. 11D-11F show profile cross-section of actin in the white block in FIGS. 11A-11C, respectively.

FIG. 12A shows imaging of an actin fluorescent probe based on Atto 488, and FIG. 12B shows imaging of GFP-actin, and FIG. 12C shows imaging of EGFP-Lifeact.

Figure 7:
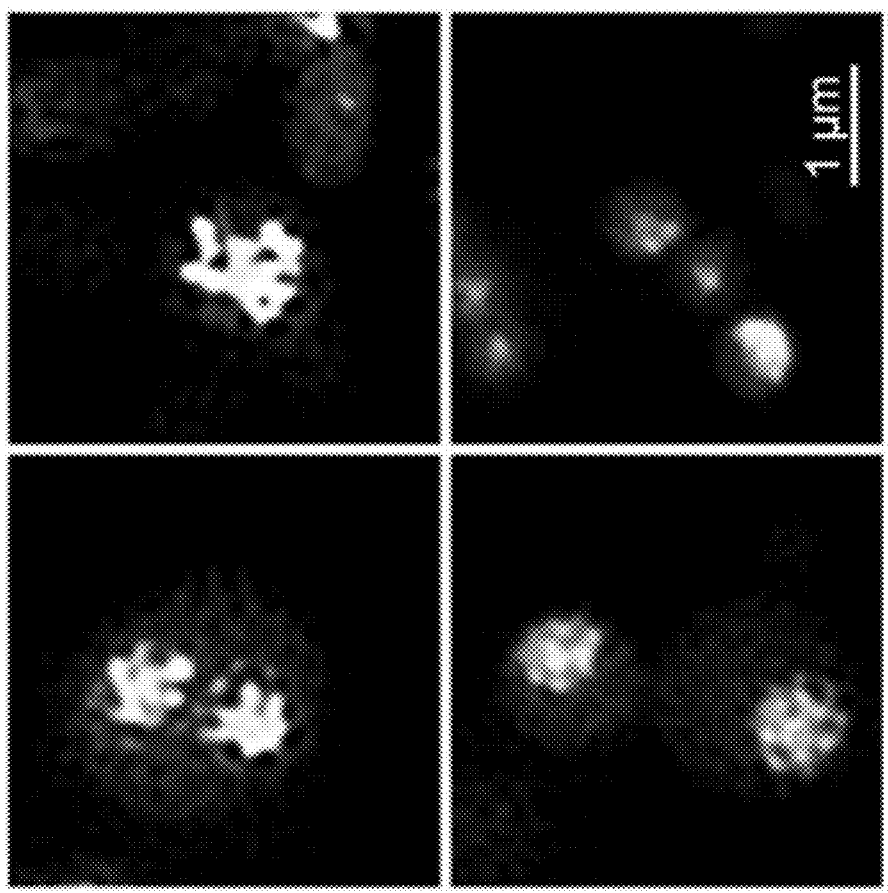
FIG. 7 shows an uneven distribution of cysteine protease C1 fluorescent probe based on Atto 565 in lysosomes in super-resolution imaging by structural illumination microscopy.

In the drawings, the scale bars of FIG. 3, FIG. 9 and FIG. 10 are 20 μm, the scale bar of FIG. 4 is 10 μm, the scale bars of FIG. 5, FIG. 6 and FIG. 11 are 5 μm, and the scale bars of FIG. 7 and FIG. 8 are given in the images.

DETAILED DESCRIPTION

To further illustrate, embodiments detailing a peptide, a fluorescent probe comprising the same, and preparation method thereof are described below. It should be noted that the following embodiments are intended to describe and not to limit the disclosure.

The peptide provided by the disclosure comprises a first peptide fragment and a second peptide fragment. The first peptide fragment comprises $(KG)_n$ or $(GK)_n$ where n is an integer between 2 and 5, K represents a lysine residue, and G represents a glycine residue; the first peptide fragment and the second peptide fragment are connected by 1-2 glycine residues.

The lysine residue is adaptive to provide a side-chain free amino group to bond to a fluorescent dye comprising an N-hydroxysuccinimide (NHS) active group; in amino acids with free amino groups on side chains, the side chain of lysine K is simple in structure, and can bond to a fluorescent dye with an NHS active group, without interference from other side chain groups.

In the interval repetition sequence of lysine residues and glycine residues, a plurality of lysine residues is adaptive to solely or multiply load the fluorescent dyes and can be compatible to various fluorescent dyes, so that the fluorescent dyes can be adaptively loaded to the lysine residue with the optimal steric hindrance. The repetition number determines the loading capability and loading efficiency of the peptide and the performance of the synthesize probe. The number of repetitions is between 2 and 5, preferably, 3. The larger the n value is, the more beneficial the loading of the fluorescent dye is, and the higher the cost is. In view of the fluorescent properties of the loaded fluorescent dye, including brightness, and antiphotobleaching capability, n value is preferable between 2 and 5. The first peptide fragment can be $(KG)_n$ or $(GK)_n$, and bonds to the second peptide fragment. G is a glycine residue, and serves as a connection part to overcome steric hindrance, and it can be determined according to the sizes of the dye molecules that one glycine as a connection part can overcome the steric hindrance, balance the probe volume and membrane penetrating efficiency, and prevent reduction of membrane penetrating efficiency caused by a too-long connection group.

The second peptide fragment is an identification sequence of cysteine protease C1 or actin. The identification sequence of the cysteine protease C1 is preferably

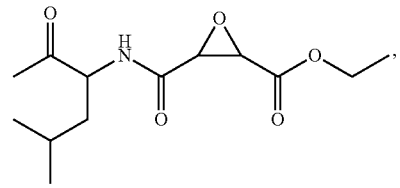 [SMILES: CCOC(=O)C1OC1C(=O)NC(CC(C)C)C(C)=O]

which
can identify the cysteine protease C1 in the lysosome, with good specificity, and can be used for purification and mass spectrum identification of a target protease. The identification sequence of the actin is preferably MGVADLIKKFE-SISKEE (SEQ ID NO: 2) which is a marker of actin fiber in a living cell.

The peptide further comprises a connection peptide and a cell-permeable peptide fragment, and their connection order can be adjustable for facilitating the synthesis of the peptide.

The connection peptide comprises one or two glycine residues.

To acquire a super-resolution image of sub-cellular structures inside a living cell, the peptide further comprises a cell-permeable peptide fragment, and the connection order thereof can be adjustable for facilitating the synthesis of the peptide. The cell-permeable peptide fragment is preferably octameric arginine and has a sequence rRrRrRRR (SEQ ID NO: 1), where, r is D-arginine, and R is L-arginine. The cell-permeable peptide fragment allows the fluorescent probe to directly penetrate cell membrane rather than entering a cell in a manner of endocytosis, has efficient cell-permeable capability, and can allow the probe to be effectively positioned on a target inside a living cell.

Considering the length of the probe and the balance between the synthesis cost and steric hindrance, the connection peptide has only one glycine G in a cell-permeable fluorescent probe for actin fiber; while in the cell-permeable fluorescent probe for the cysteine protease C1 in the lysosomes, two glycines G are added between rRrRrRRR (SEQ ID NO: 1) and the identification group.

The peptide is synthesized by using solid-phase peptide synthesis.

The fluorescent probe comprises the peptide provided by the disclosure. The lysine residue of the peptide is coupled to a fluorescent dye. The fluorescent dye is a fluorescent dye comprising an NHS active group, and preferably, is Alexa Fluor 647 NHS ester, Cy3B NHS ester, Atto 565 NHS ester and/or Atto 488 NHS ester.

The peptide can be widely adapted to various commercialized fluorescent dyes. When the probe formed by the commercialized dye and the peptide is used for imaging in living cells, a long-term super-resolution image with good image quality can be obtained.

The fluorescent probe provided by the disclosure is prepared by coupling the peptide to a fluorescent dye. The method comprises:

(1) peptide synthesis: synthesizing the peptide by using a solid phase synthesis, the peptide being coupled to a resin;

(2) peptide purification: separating the peptide from the resin, removing a protective group of a side chain of the peptide, and purifying and concentrating the peptide;

(3) introduction of fluorescent dye: covalently connecting free amino groups of the lysine residue of the peptide obtained in 2) to an NHS active group of the fluorescent dye by using a liquid phase reaction to obtain the fluorescent probe; and (4) fluorescent probe purification: dissolving the fluorescent probe obtained in 3), and purifying the fluorescent probe with reversed-phase chromatography.

The fluorescent probe is a combination of a peptide fragment and a fluorescent dye, and the amount of the fluorescent dye needed is relatively low. This reduces the cost of the probe, and the selection of the fluorescent dye is flexible.

Example 1

A peptide has a formula I:

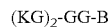 (I)

where, K is a lysine residue, G is a glycine residue, B is a second peptide fragment.

The peptide fragment B comprises a connection peptide and a recognition unit.

The recognition unit is MGVADLIKKFESISKEE (SEQ ID NO: 2).

The peptide is prepared by solid phase peptide synthesis.

Example 2

A peptide has a formula II:

 (II)

where, K is a lysine residue, G is a glycine residue, B is a second peptide fragment.

The peptide fragment B comprises a connection peptide, a recognition unit, and a cell-permeable peptide fragment.

The recognition unit is:

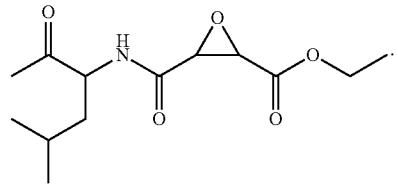 [SMILES: CCOC(=O)C1OC1C(=O)NC(CC(C)C)C(C)=O]

The cell-permeable peptide fragment is octameric arginine, and has a sequence rRrRrRRR, wherein, r is D-arginine, and R is L-arginine.

The peptide is prepared by solid phase peptide synthesis.

Example 3

A peptide has a formula III:

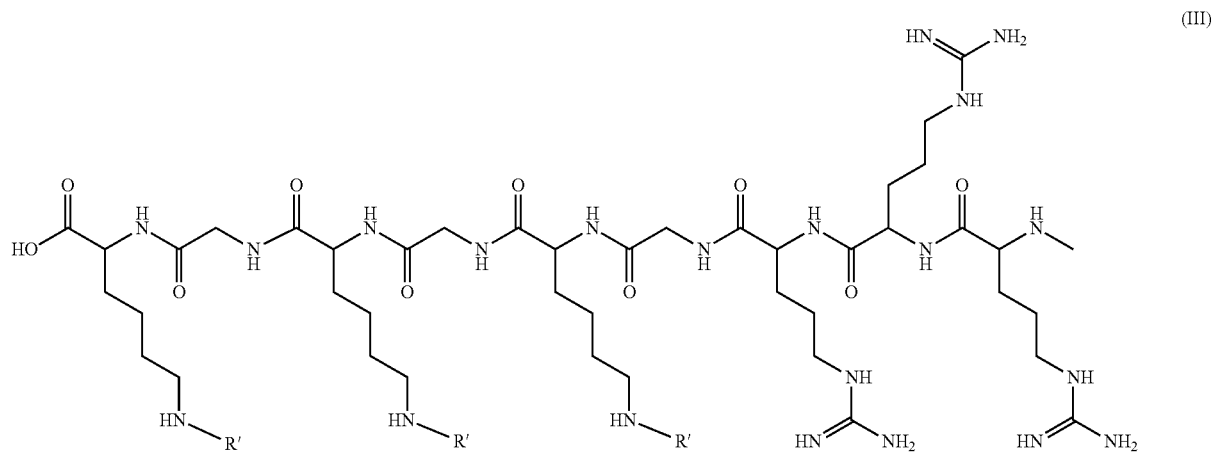

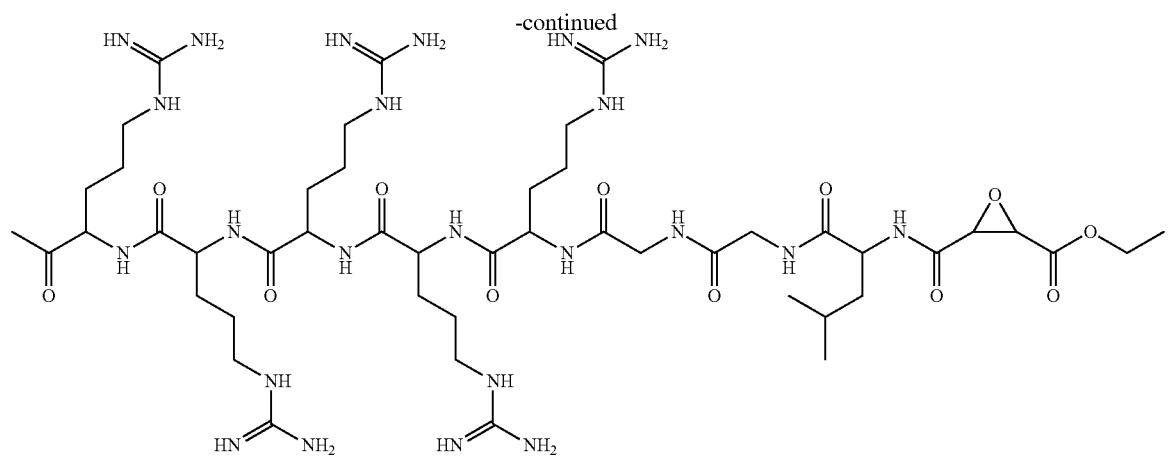
The connection peptide is GG.
The recognition unit is
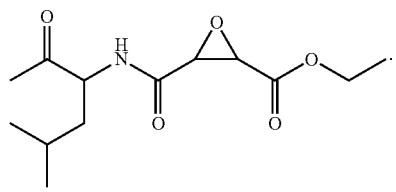 [SMILES: CCOC(=O)C1OC1C(=O)NC(CC(C)C)C(C)=O]
The cell-permeable peptide fragment is octameric arginine, and has a sequence rRrRrRRR, where, r is D-arginine, and R is L-arginine.
The peptide is prepared according to the following flow chart:
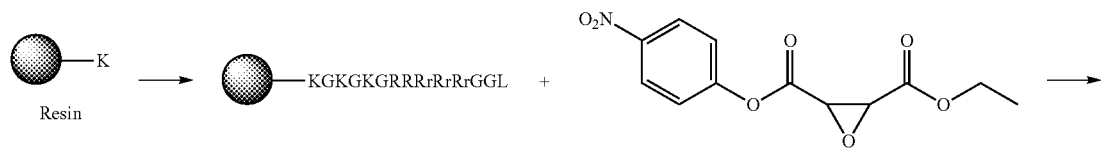
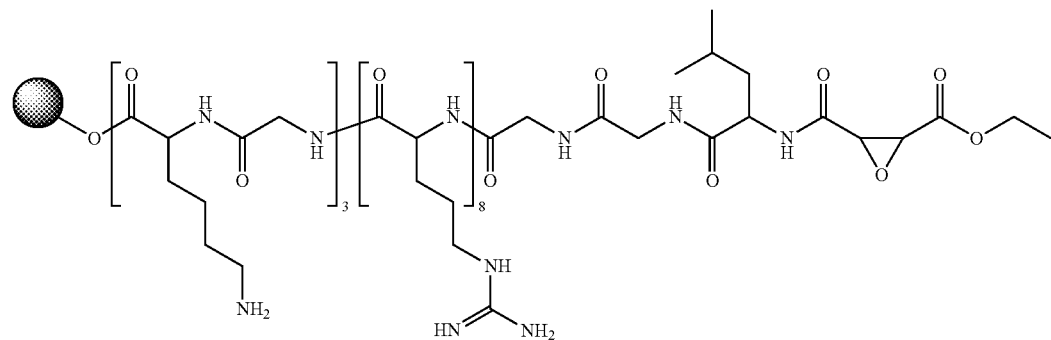

Figure 1:
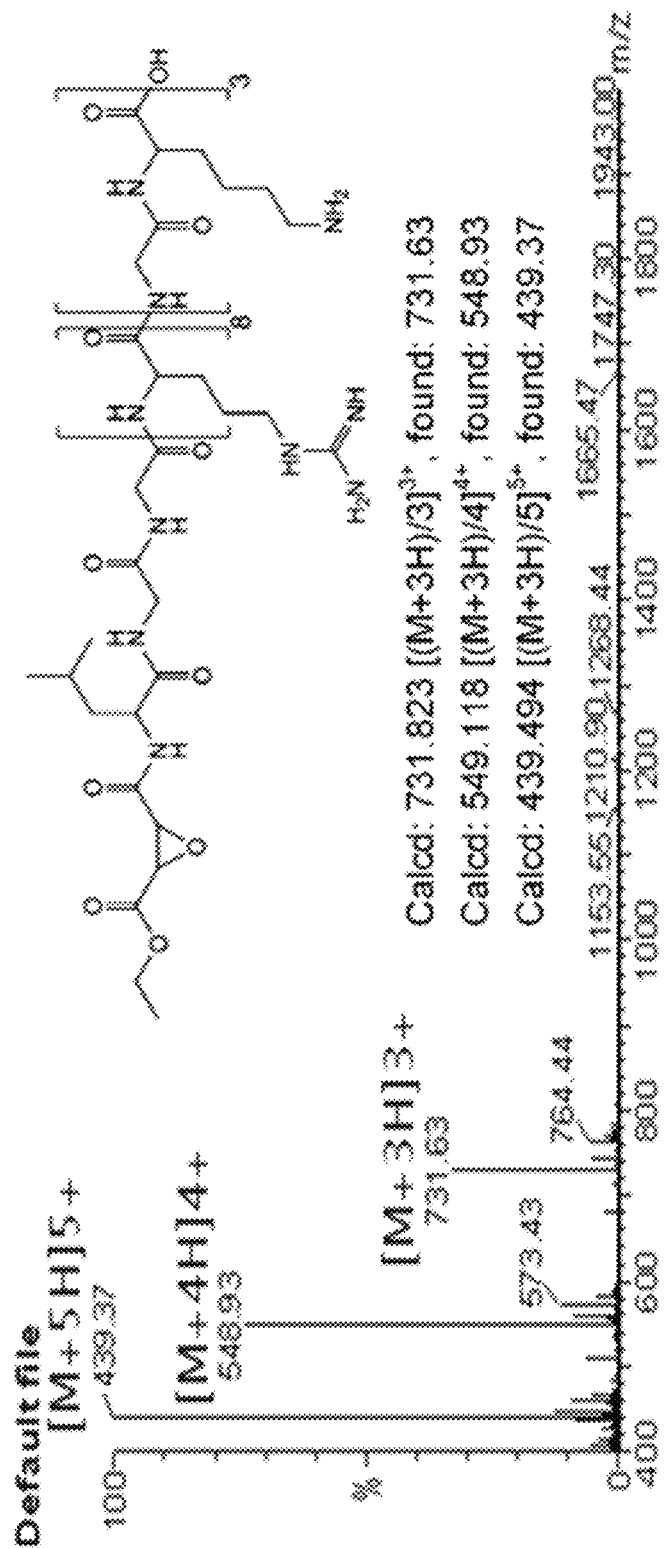
FIG. 1 is a mass spectrometry (MS) detection result of a peptide provided in Example 3.

The peptide is prepared by solid phase peptide synthesis, and the mass spectrometry (MS) detection report thereof is shown in FIG. 1.

Example 4

A peptide has a formula IV:

B-G-(KG)₃-P        (IV)

where, K is a lysine residue, G is a glycine residue, B is a second peptide fragment, and P is a cell-permeable peptide fragment.

The second peptide fragment is MGVADLIKKFESISKEE (SEQ ID NO: 2).

The cell-permeable peptide fragment is octameric arginine, and has a sequence rRrRrRRR, wherein, r is D-arginine, and R is L-arginine.

The peptide is shown in a formula as follows: MGVADLIKKFESISKEEGKGKGKGrRrRrRRR SEQ ID NO: 3.

The peptide is synthesized according to the following flow chart:

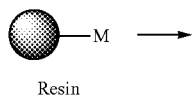
Resin

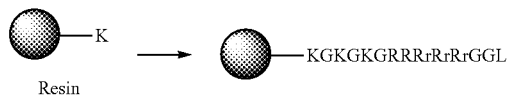

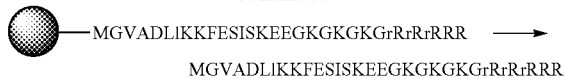

Figure 2:
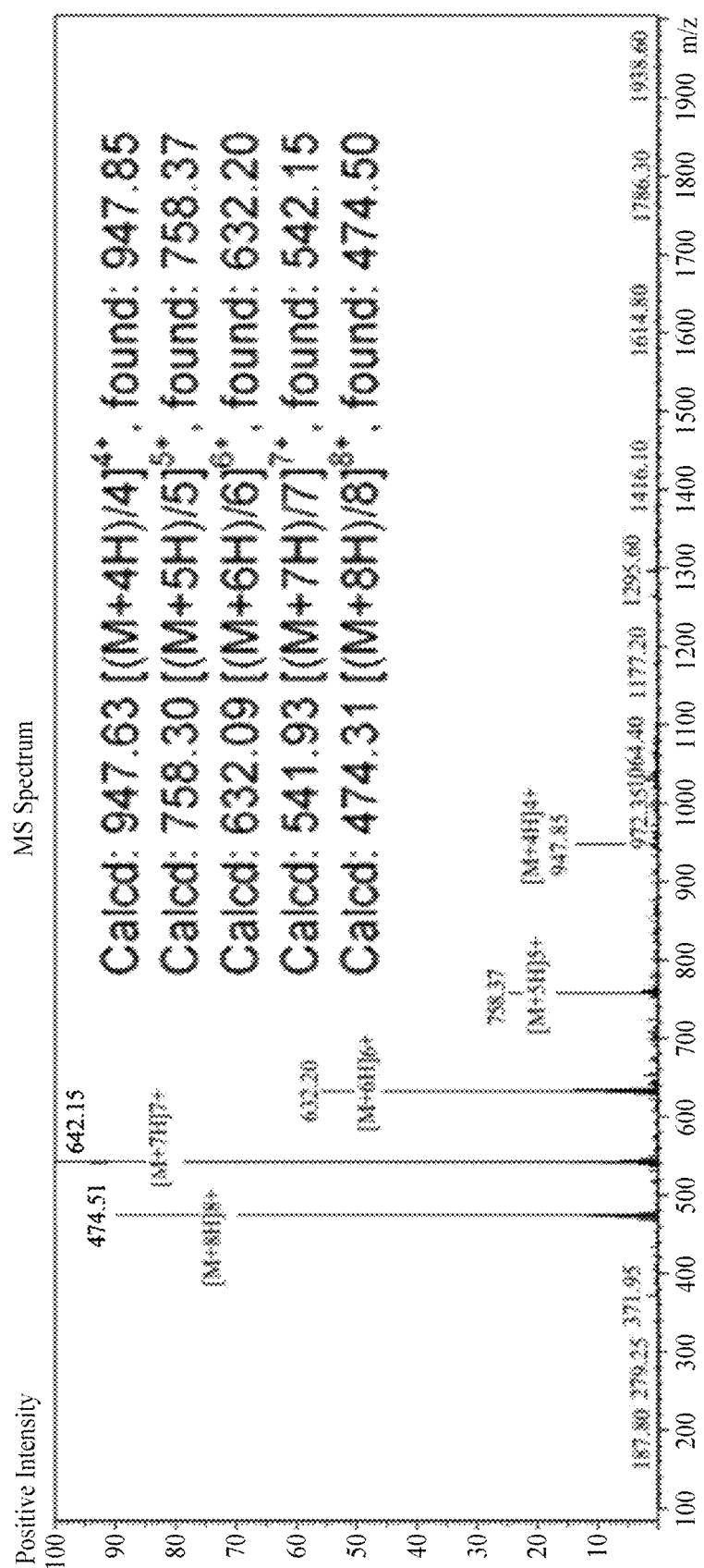
FIG. 2 is a mass spectrometry detection result of a peptide provided in Example 4.
Figure 3C:
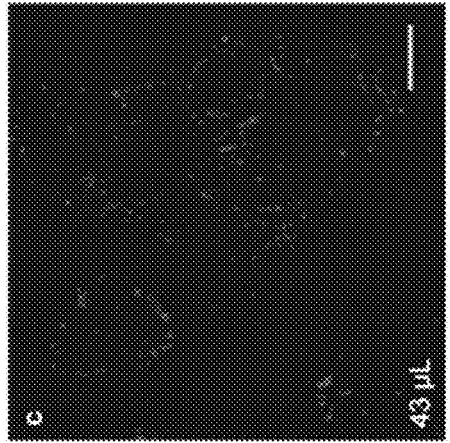
FIGS. 3A-3F show labeling of a lysosome by Alexa Fluor 647-based fluorescent probes at different concentrations, where the total volume is 1000 µL, in FIG. 3A, the mother liquor of the probe is 14 µL.
Figure 3B:
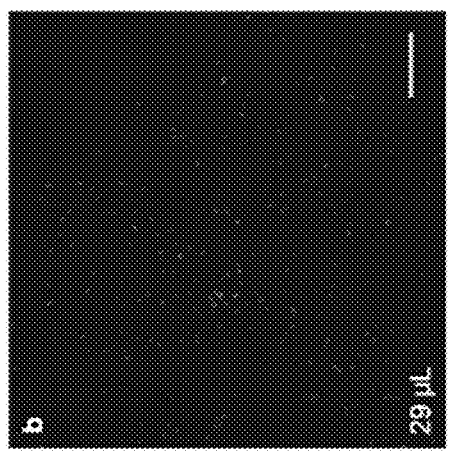
Figure 3A:
Figure 3F:
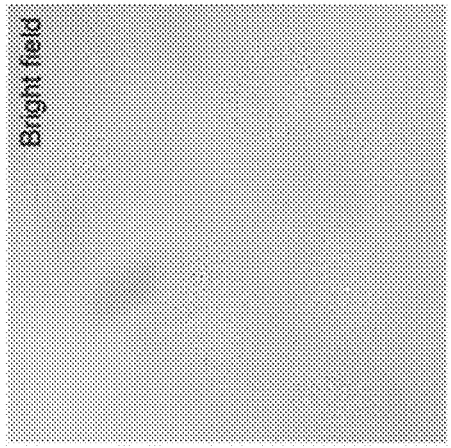
Figure 3E:
Figure 3D:
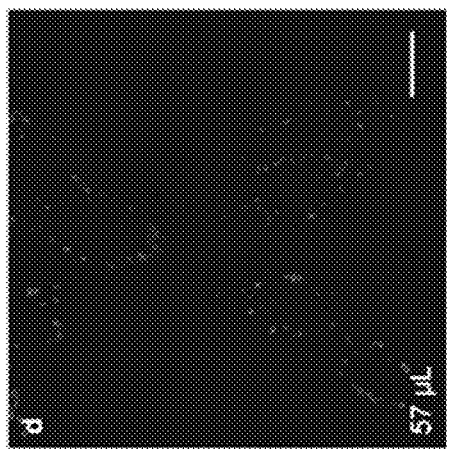

The peptide is prepared by solid phase peptide synthesis, and the mass spectrometry (MS) detection report thereof is shown in FIG. 2.

Example 5

A fluorescent probe comprises the peptide provided in Example 3. The lysine residue of the peptide is coupled to a fluorescent dye. The fluorescent dye is Alexa Fluor 647 NHS ester, Atto 565 NHS ester or Atto 488 NHS ester, which are respectively named cysteine protease C1 fluorescent probe based on Alexa Fluor 647, cysteine protease C1 fluorescent probe based on Atto 565, and cysteine protease C1 fluorescent probe based on Atto 488.

The fluorescent probe is synthesized according to the following method:

(1) Peptide synthesis: sequentially connecting small molecules or amino acids with protected side chains by a solid-phase synthesis method, the peptide being coupled to a resin.

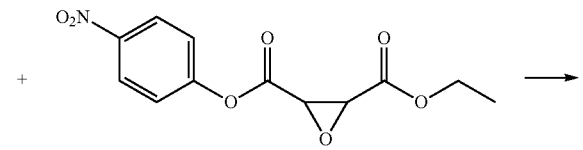

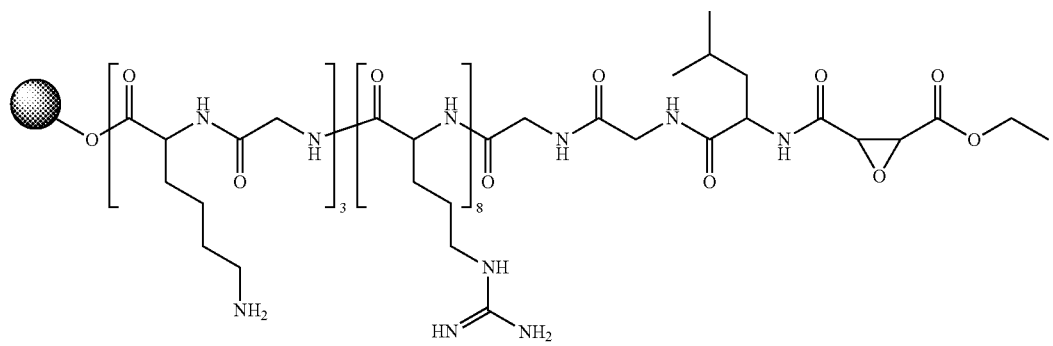

(2) Peptide purification: removing the protection of the amino acid side chain and separating the peptide from the resin, purifying the peptide via HPLC to above 95% purity, collecting product components and then freeze drying, and concentrating to obtain a peptide fragment crystal.

(3) Connection of fluorescent dye:

dish (glass bottom dish Φ15 mm, NEST Biotechnology Co., LTD., China), cultured overnight in a McCoy's 5 A culture medium containing 10% fetal calf serum at 37° C. in the presence of 5% $CO_2$.

Probe incubation: prior to the experiment, the culture medium in the confocal glass bottom dish was removed out,

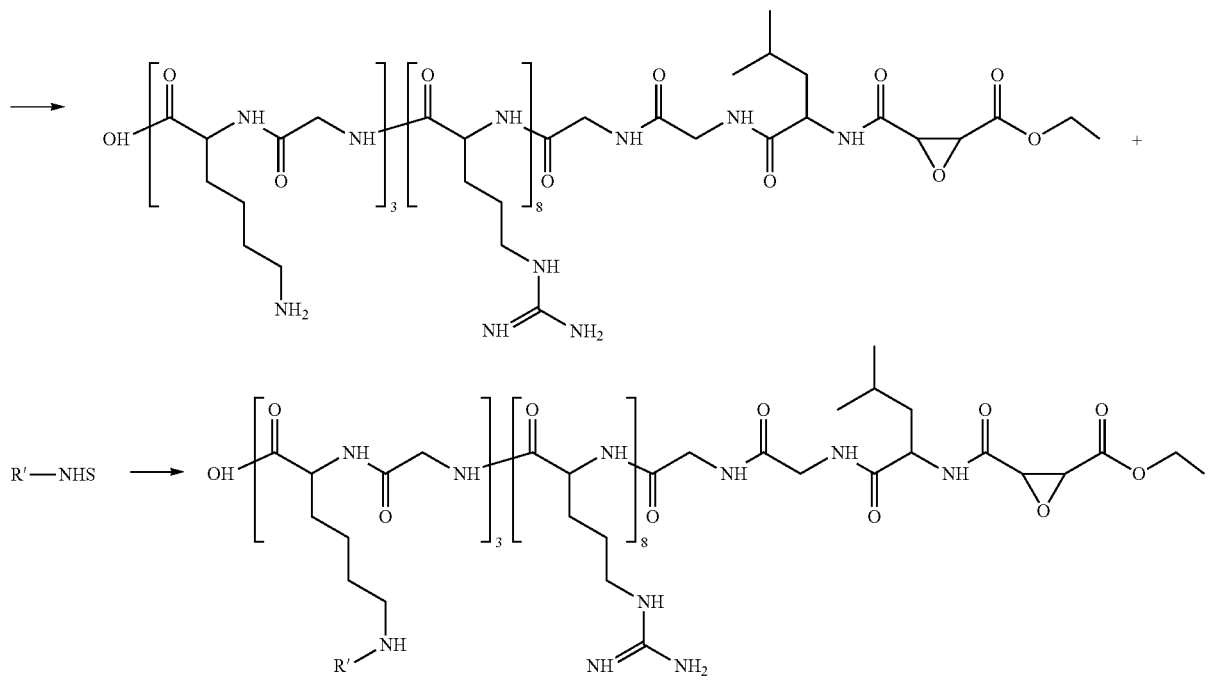

Specifically, free-dye probe powder was dissolved in 0.1 M $NaHCO_3$ solution, the final concentration of the solution was 0.5 mM. The solution was filtered and sterilized. The purchased Alexa Fluor 647 NHS ester (1 mg, Thermo Fisher Scientific, Inc.), Atto 565 NHS ester (1 mg, Sigma-Aldrich Co., LLC) or Atto 488 NHS ester (1 mg, Sigma-Aldrich Co., LLC) dyes were dissolved with anhydrous DMSO and then packaged into about 30 nmol/tube. The solvents in the tubes were removed, and the dyes were preserved at −20° C. in the dark. One tube of packaged dyes was dissolved in 20 µL of anhydrous DMSO, and then the obtained solution was dropwise added to 28 µL of the mother liquor of the free-dye probe, uniformly mixed, shaken for more than 2 h in the dark.

(4) Fluorescent probe purification: pumping out the liquid in the reaction system, dissolving the probe with an aqueous solution containing 0.5% TFA and 5% acetonitrile, and carrying out column chromatography with a C18 reverse column. The eluant was 20 µL of an acetonitrile aqueous solution system having a purity of 50-80%; the product components were combined and the liquid was removed to obtain a product crystal. The crystal was added to 200 µL of PBS solution, and stored in 4° C. refrigerator for use.

According to the aforesaid operations, the cysteine protease C1 fluorescent probe based on Alexa Fluor 647, the cysteine protease C1 fluorescent probe based on Atto 565, and the cysteine protease C1 fluorescent probe based on Atto 488 were respectively prepared.

The imaging experiment of the fluorescent probe provided by this example is as follows:

Cell preparation: U2OS cells ($2 \times 10^4$ cells/well) in a growth state were inoculated to sterile confocal glass bottom and residual serum was washed with PBS solution. 14-71 µL of the mother liquor was diluted with PBS solution until the final volume was 100 mL. The diluted solution was added to a confocal glass bottom dish and incubated for 30 min at 37° C. in the presence of 5% $CO_2$. The probe solution was removed, and 200 µL of 1 mg/mL typan blue solution was added. After 1 min, the typan blue solution was removed, the cells were washed three times with PBS solution and provided with a phenol red-free DMEM culture medium containing 10% fetal calf serum, and the culture medium was observed under an imaging system.

Imaging by laser scanning confocal microscopy: a laser scanning confocal microscope LSM 710 (Zeiss, German) was used. The maximum excitation wavelength of Alexa Fluor 647 was 650 nm and the maximum emission wavelength 665 nm; the maximum excitation wavelength of LysoTracker Red was 577 nm and the maximum emission wavelength 590 nm. The cells were labelled by the cysteine protease C1 fluorescent probe based on Alexa Fluor 647, and the laser scanning confocal images were shown in FIGS. 3A-3F. As shown in FIGS. 3A-3F, when the amount of the mother liquor of the probe was in the range from 14 to 71 µL, the probe solution can smoothly label dotted structures in the cells; meanwhile, by using the typan blue solution, the cells were unstained blue, which proved the activity of the cells. FIG. 4A showed a dotted structure labeled by the cysteine protease C1 fluorescent probe based on Alexa Fluor 647, which was consistent with the labeling result of LysoTracker Red in FIG. 4B. In the colocalization image of two channels shown in FIG. 4C, two channels could be used for jointly positioning, proving that the dotted structure labeled by the cysteine protease C1 fluorescent probe based on Alexa Fluor 647 was a lysosome of a living cell.

Preparation of imaging buffer for live-cell stochastic optical reconstruction microscopy (STORM): a) buffer A (pH 8.0) containing 10 mM Tris and 50 mM NaCl; b) Catalase solution was dissolved in the buffer A and the final concentration thereof was 17 mg/L. The diluted solution was packaged into 10 μL/tube and then stored at −20° C.; c) Glucose Oxidase solution was dissolved in the buffer A, and the final concentration thereof was 70 mg/mL, then the diluted solution was packaged into 40 μL/tube and then stored at −20° C.; d) 1 M mercaptoethylamine (MEA) solution was dissolved in 0.25 N hydrochloric acid solution, and the final concentration thereof was 70 mg/mL. The diluted solution was stored at −20° C.; e) GLOX solution: uniformly mixing one tube of solution from c) and d), totaling 50 μL, and the mixed solution was preserved at 4° C. for 2 weeks for use; f) living cell imaging buffer: 0.0125 g of HEPES (final concentration was 75 mM) and 0.014 g of Glucose (final concentration was 2%) were dissolved in 700 μL of DMEM culture medium; g) living cell imaging buffer for STORM: 1.2 μL of MEA solution and 2 μL of GLOX solution were respectively added to 200 μL of the living cell imaging buffer, and the period of validity of the obtained solution was 60 min.

Figures 5A, 5B:
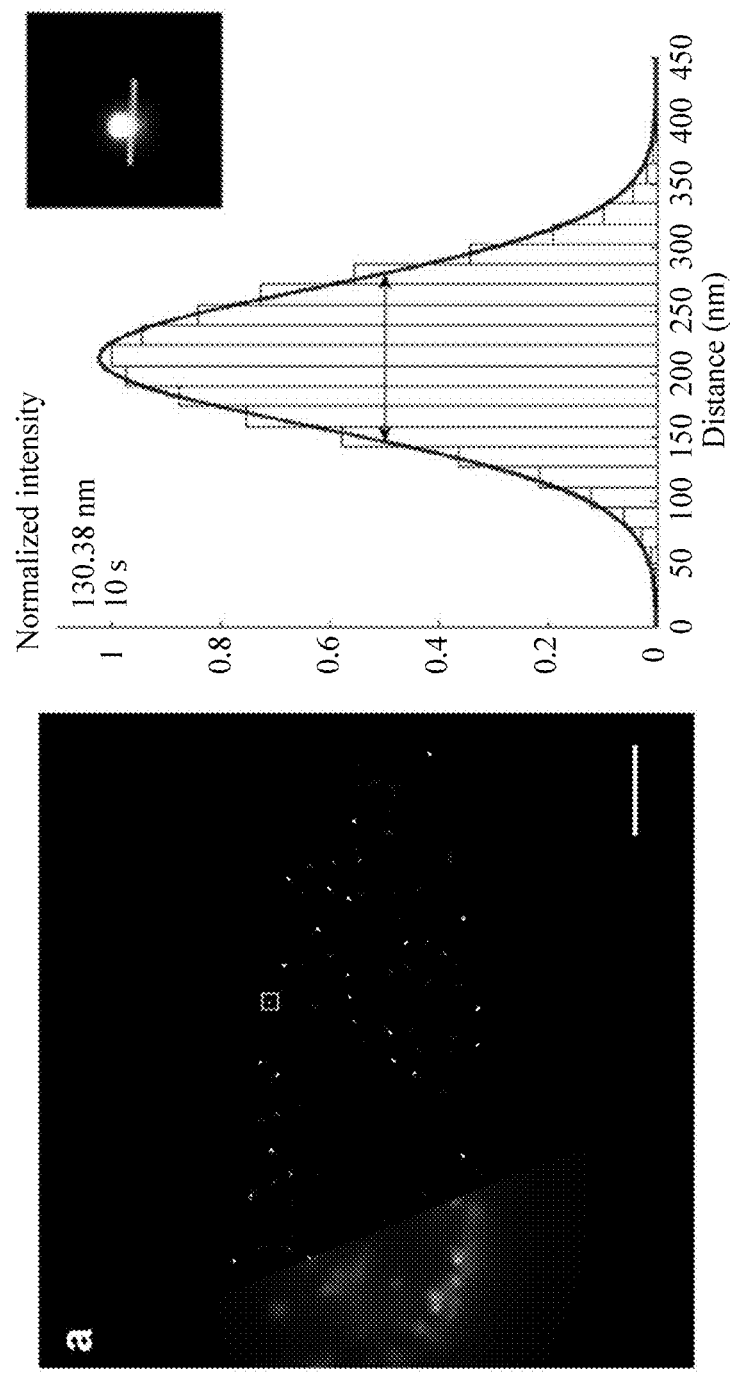
FIGS. 5A-5B show super-resolution imaging by stochastic optical reconstruction microscopy of cysteine protease C1 fluorescent probe based on Alexa Fluor 647, where.

Super-resolution imaging by stochastic optical reconstruction microscopy: a super-resolution microscope N-STORM (Nikon, Japan) was employed. The maximum excitation wavelength of Alexa Fluor 647 was 650 nm and the maximum emission wavelength was 665 nm. The laser power was determined according to the following method: a cell sample was placed on a carrier and fixed with a clamp. The focal surface was first found in the bright field of vision, and then mercury lamp was combined with a corresponding filter to find the field with clear marks and high signal background ratio. Mercury lamp was quickly turned off to reduce fluorescence quenching of the sample. Selecting an appropriate excitation wavelength, observing with a very small power (the fluorescent sample in the field of vision can be seen), adjusting the appropriate total internal reflection fluorescence (TIRF) angle to obtain an image with the best signal background ratio. The power of the excitation light was slowly improved. When the power of the excitation light exceeded a certain threshold, fluorescent molecules in the view started blinking, and the laser power used in this moment, namely, the default power of the current probe, was recorded. The image was processed by using a low-density localization reconstruction algorithm according to the blinking degree of the sample to obtain a stochastic optical reconstruction super-resolution images (FIGS. 5A-5B). FIGS. 5A-5B showed that compared with the total internal reflection images prior to calculation (left bottom), the resolution of the stochastic optical reconstruction image (top right) was effectively improved. The lysosome labeled by white boxes in the drawing had a full width at half maximum of 130.38 nm, which was less than 200 nm, so it was an effective super-resolution image. This experiment proves that the cysteine protease C1 fluorescent probe based on Alexa Fluor 647 has an ability to realize the super-resolution imaging under stochastic optical reconstruction microscopy, and can obtain a live-cell super-resolution image of lysosomes.

Super-resolution imaging by structural illumination microscopy: super-resolution microscope N-SIM (Nikon, Japan) was employed. The maximum excitation wavelength of Alexa Fluor 647 was 650 nm and the maximum emission wavelength was 665 nm; the maximum excitation wavelength of LysoTracker Red was 577 nm and the maximum emission wavelength of LysoTracker Red was 590 nm; the maximum excitation wavelength of Atto 565 was 563 nm and the maximum emission wavelength of Atto 565 was 592 nm; the maximum excitation wavelength of Atto 488 was 501 nm and the maximum emission wavelength was 523 nm. A sample was photographed using a 2D-SIM mode, one SIM result was calculated from 9 original images (three angles, three phases), and the exposure time of each original image was 30 ms. Considering quick movement ability of a lysosome in living cells, single-color imaging interval time was set as 1 s so as to continuously photograph cells at above 300 frames. After the capturing was completed, the average time interval among various SIM images was about 1.15 s. In a double-color imaging experiment for the cysteine protease C1 fluorescent probe based on Alexa Fluor 647 and a standard lysosome marker Lyso Tracker Red, considering the module conversion speed of the imaging system, the imaging time interval was set as 6 s.

Based on a time-lapsed SIM imaging, take the center of the lysosome as a reference, the coordinates of lysosomes were recorded using ImageJ software, and trace charts of 101 lysosomes in four U2OS cells on the confocal surface were drawn using MATLAB (FIGS. 6A-6H). It can be seen from FIGS. 6A-6H that there were many movement types of lysosomes: (i) movement routes of some lysosomes were long and complex, they might undergo one quick and directional movement and then were subjected to complicated multi-direction movements within a certain range; thereafter, these lysosomes might be either stabilized, or reaccelerated toward a certain direction (such as two red lines in FIG. 6B); (ii) some lysosomes underwent a movement similar to free diffusion in a certain region, the diffusion distance was not as far as that of the first type, and the speed was slower than that of the first type; the direction was uncertain, and the movement track was like scattered woolen yarn (such as orange lines in FIG. 6C); (iii) also, one type of lysosomes almost had no displacement, and only performed extremely tiny movement in situ, in consideration of error of manual tracing, this type of lysosomes were almost static (tracks almost having no displacement were shown in FIGS. 6A-6D, for example, as shown in top right of FIG. 6C). Although it can be seen from the above analysis that most lysosomes were in a relatively stable state, a small amount of lysosomes still had quick movement and large displacements, and the movement details were possibly lost if the imaging speed was too slow or the exposure time was too short. Experiments showed that the cysteine protease C1 fluorescent probe based on Alexa Fluor 565 has appropriate brightness and anti-bleaching capability, has a strong potential in quick and long-term super-resolution imaging.

The cysteine protease C1 fluorescent probe based on Alexa Fluor 565 can be applied to tracing of the lysosome. In addition, the probe can specifically label the cysteine protease C1 in the lysosome, so the distribution of the cysteine protease C1 in the lysosome can be determined according to uneven distribution of the fluorescent probe intensity in the lysosome. Apart from uniform fluorescence distribution patterns of most lysosomes in FIGS. 6A-6H, FIG. 7 showed certain uneven fluorescence distribution: two bright spots, one irregular bright spot, one round bright spot or half-moon bright spot in one lysosome. These bright spots were extremely distinct in the round or elliptical outline of the whole lysosome, and can move in the lysosome along with movement or shaking of the lysosome. The uneven distribution of fluorescence in these lysosomes was likely to imply different contents and distributions of the cysteine protease C1 in different lysosomes. In view of importance of the cysteine protease C1 in the lysosomes, these results suggest that their abilities of digesting substrates were different. This experiment proved that the cysteine protease C1 fluorescent probe based on Alexa Fluor 565 had excellent image quality in structural illumination super-resolution imaging, and can depict uneven distribution of the cysteine protease C1 in the lysosome.

As shown in FIG. 8A, apart from labeling the lysosome, LysoTracker Red was unevenly distributed in the cytosol near the nucleus. It can be seen from the labeling of the cysteine protease C1 fluorescent probe based on Alexa Fluor 647 in FIG. 8B that as long as the lysosomes were located on the confocal plane, they had clear boundaries. The background difference of two images was shown in FIGS. 8A2 and FIG. 8B2 obtained by time-lapsed imaging. During movement, the lysosome labeled by the cysteine protease C1 fluorescent probe based on Alexa Fluor 647 had a clear outline and an obvious shape, while the lysosome labeled by LysoTracker Red was in a fuzzy background. Here, it should be noted that some lysosomes were oval during movement, mainly because of the quick movement of lysosomes, which was relatively common in the lysosomes in SIM imaging, but was difficultly found in traditional imaging. To prove the specificity of the lysosome probe was not accidental, the cysteine protease C1 fluorescent probe based on Alexa Fluor Atto 565 and the cysteine protease C1 fluorescent probe based on Alexa Fluor Atto 488 were used to label U2OS cells. It can be seen from FIGS. 8C-8D that the lysosomes labeled by two probes also had clear boundary outlines.

Based on these results, it can be seen that the uneven background of LysoTracker Red was very obvious, while the cysteine protease C1 fluorescent probes based on Alexa Fluor 647, the cysteine protease C1 fluorescent probe based on Atto 565 and the cysteine protease C1 fluorescent probe based on Atto 488 had almost no detectable backgrounds, proving that the three lysosome-directed cell-permeable fluorescent probes were more suitable to label lysosome than LysoTracker Red in the structural illumination super-resolution imaging.

Example 6

A fluorescent probe comprises the peptide provided in Example 4. The lysine residue of the peptide is coupled to a fluorescent dye. The fluorescent dye is Alexa Fluor 647 NHS ester, Cy3B NHS ester, or Atto 488 NHS ester, which are respectively named actin fluorescent probe based on Alexa Fluor 647, actin fluorescent probe based on Cy3B, and actin fluorescent probe based on Atto 488.

The fluorescent probe is synthesized according to the following method:

(1) Peptide synthesis: sequentially connecting small molecules or amino acids with protected side chains by a solid-phase synthesis method, the peptide being coupled to a resin.

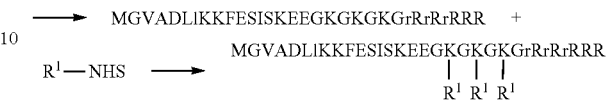

(2) Peptide purification: removing the protection of the amino acid side chain and separating the peptide from the resin, purifying the peptide via HPLC to above 95% purity, collecting product components and then freeze drying, and concentrating to obtain a peptide fragment crystal.

(3) Connection of fluorescent dye:

→ MGVADLIKKFESISKEEGKGKGKGrRrRrRRR +

R¹—NHS → MGVADLIKKFESISKEEGKGKGKGrRrRrRRR
            |  |  |
            R¹ R¹ R¹

Specifically, free-dye probe powder was dissolved with 0.1 M NaHCO₃ solution, and the final concentration of the solution was 0.5 mM. The solution was filtered and sterilized. The purchased Alexa Fluor 647 NHS ester (1 mg, Thermo Fisher Scientific, Inc.), Cy3B NHS ester (1 mg, GE Healthcare shanghai Co., Ltd) or Atto 488 NHS ester (1 mg, Sigma-Aldrich Co., LLC) dyes were dissolved with anhydrous DMSO and then packaged into about 30 nmol/tube, and solvents in the tubes were removed. The dyes were preserved at −20° C. in the dark. One tube of packaged dye was dissolved in 20 μL of anhydrous DMSO. The obtained solution was dropwise added to 28 μL of the mother liquor of the free-dye probe, uniformly mixed, shaken for more than 2 h in the dark.

(4) Fluorescent probe purification: pumping the liquid out of the reaction system, dissolving the probe with an aqueous solution containing 0.5% TFA and 5% acetonitrile, and carrying out column chromatography with a C18 reverse column. The eluant was 20 μL of an acetonitrile aqueous solution system having a purity of 50-80%; the product components were combined and the liquid was removed to obtain a product crystal. The crystal was added to 200 μL of PBS solution, and stored in 4° C. refrigerator for use.

According to the aforesaid operations, the actin fluorescent probe based on Alexa Fluor 647, the actin fluorescent probe based on Cy3B, and the actin fluorescent probe based on Atto 488 were respectively prepared.

The imaging experiment of the fluorescent probe provided by this example is as follows:

Cell preparation: the same as that in Example 5.

Figures 10A, 10B, 10C:
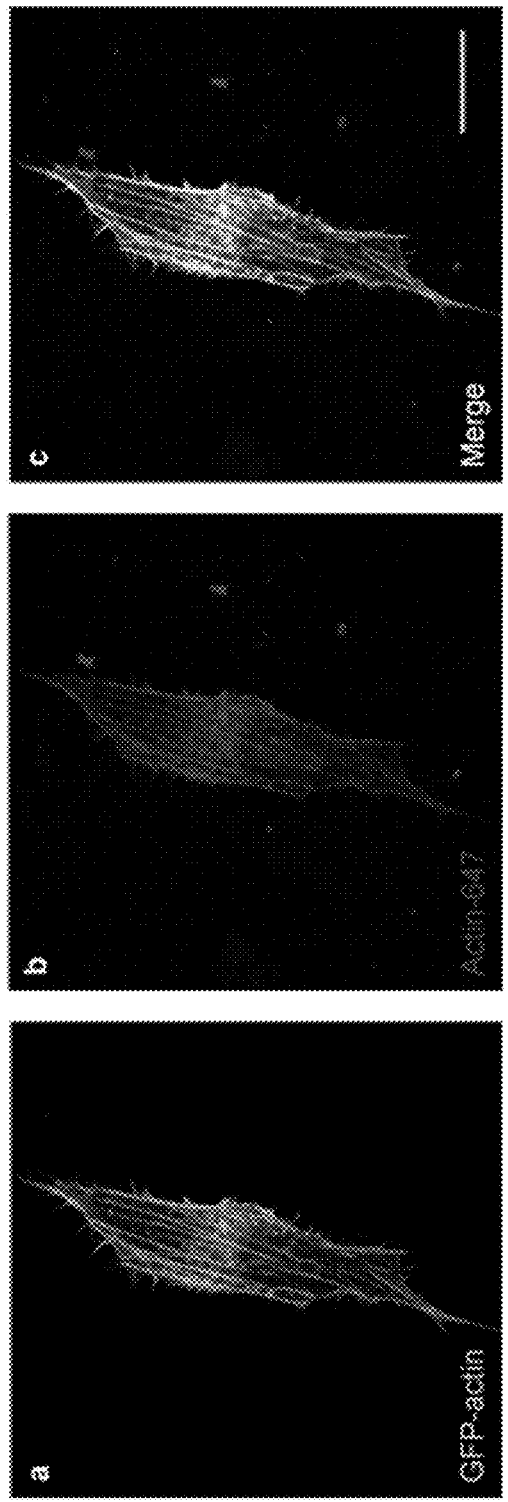
FIGS. 10A-10C show labeling of actin by Alexa Fluor 647-based fluorescent probes and standard actin marker GFP-actin in living cells, where.

Imaging by laser scanning confocal microscopy: a laser scanning confocal microscope LSM 710 (Zeiss, German) was used. The maximum excitation wavelength of Alexa Fluor 647 was 650 nm and the maximum emission wavelength 665 nm; the maximum excitation wavelength of GFP was 488 nm and the maximum emission wavelength 507 nm. Primary cultured astroglial cells (Astrocyte) were incubated with a work solution containing 21 μL of the mother liquor for 30 minutes (FIG. 9A). Most of the probes in the cells were distributed in a diffuse manner, and the filamentous markers were formed at the cell edge and filopodia. This indicated that the concentration of the probes entering the cells was insufficient to reach the threshold of identifying the Lifeact-bonding actin. And the contrast between inside and outside cells was very low due to the lack of the probes in the cells. When the amount of the probe was 36 μL (FIG. 9B), there was a clear filamentous marker in the cell, but the middle part of the cell was still blurred. At the same time, compared with the amount of the probe of 21 μL, the extracellular background was relatively low because of the stronger intracellular signal. When the amount of the probe was 43-57 μL (FIGS. 9C-9D), the brightness of filamentous structure in cells was further enhanced, while the extracellular background was almost negligible. At the same time, after incubation with high concentration of probes (57 μL), the cells in the bright field were not stained with trypan blue solution, indicating that the cells remained active after incubation with the probe. In view of the fact that the labeling of the probes had a high contrast both in and out of the cells when the dosage of the probes ranges from 43 to 57 μL, the dosage of probes was recommended to be within this range. This experiment also proved that the new microfilament probes can be used in labeling of primary astrocytes which were difficult to transfect. FIG. 10A shows a linear structure labeled by the actin fluorescent probe based on Alexa Fluor 647, which was consistent with the labeling result of GFP-actin in FIG. 10B. In a colocalization image of two channels shown in FIG. 10C, good colocalization of the two channels suggest that the structure labeled by the actin fluorescent probe based on Alexa Fluor 647 was actin filaments in live cells.

Preparation of imaging buffer of living cell for STORM: the same as that in Example 5.

Figures 11A, 11D:
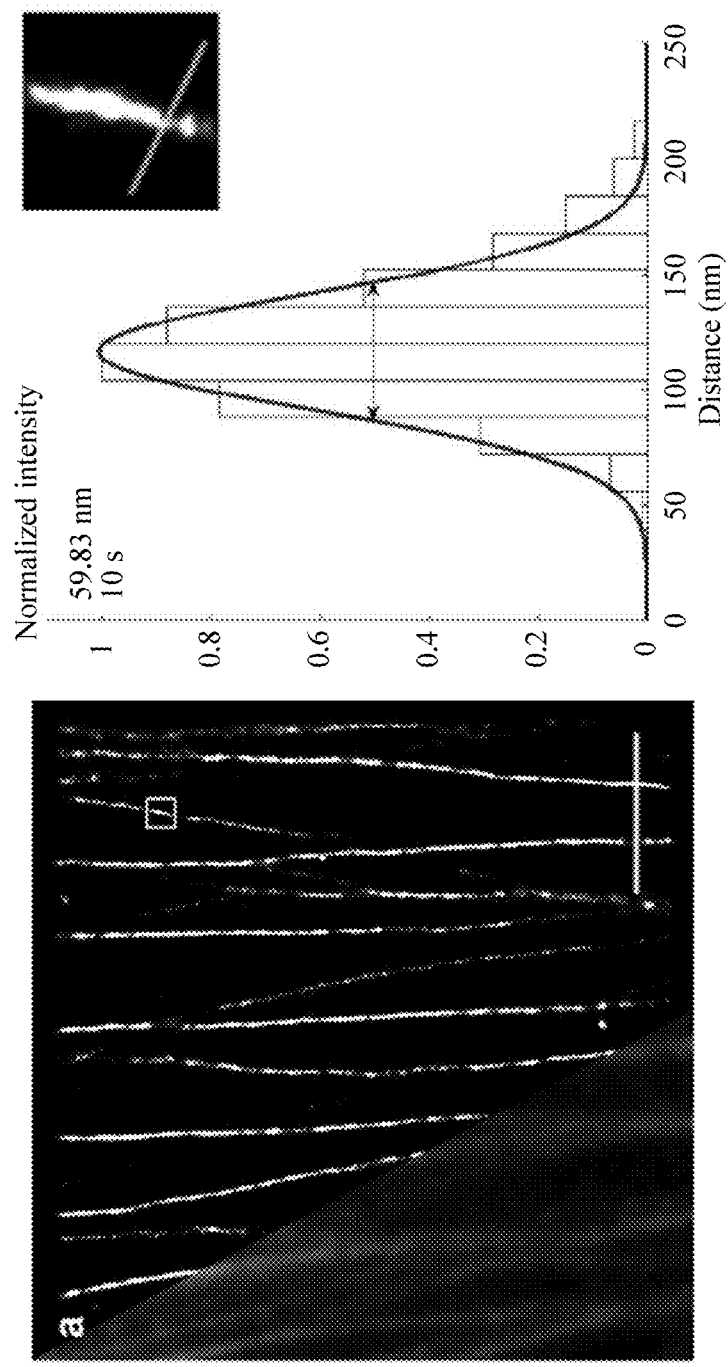
FIGS. 11A-11F show super-resolution imaging by stochastic optical reconstruction microscopy of actin fluorescent probes based on Alexa Fluor 647, Cy3B and Atto488, where.
Figures 11B, 11E:
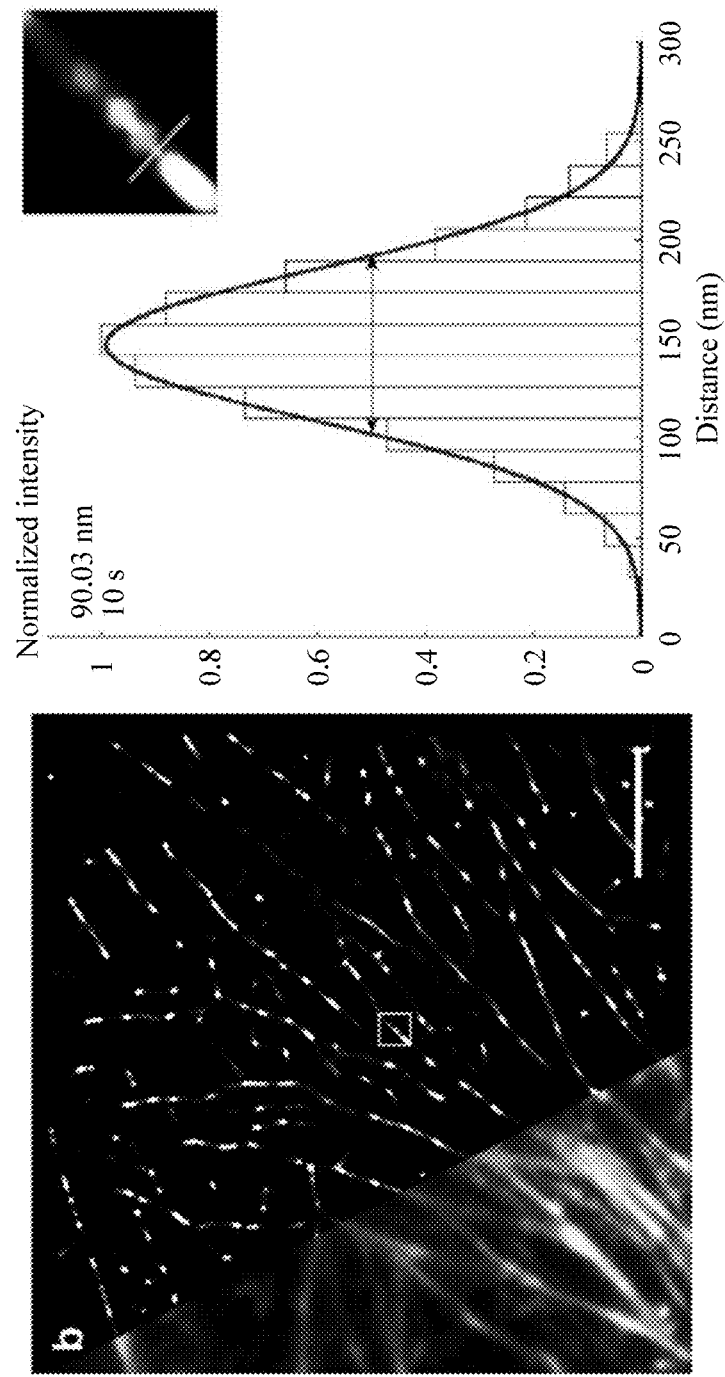
Figures 11C, 11F:
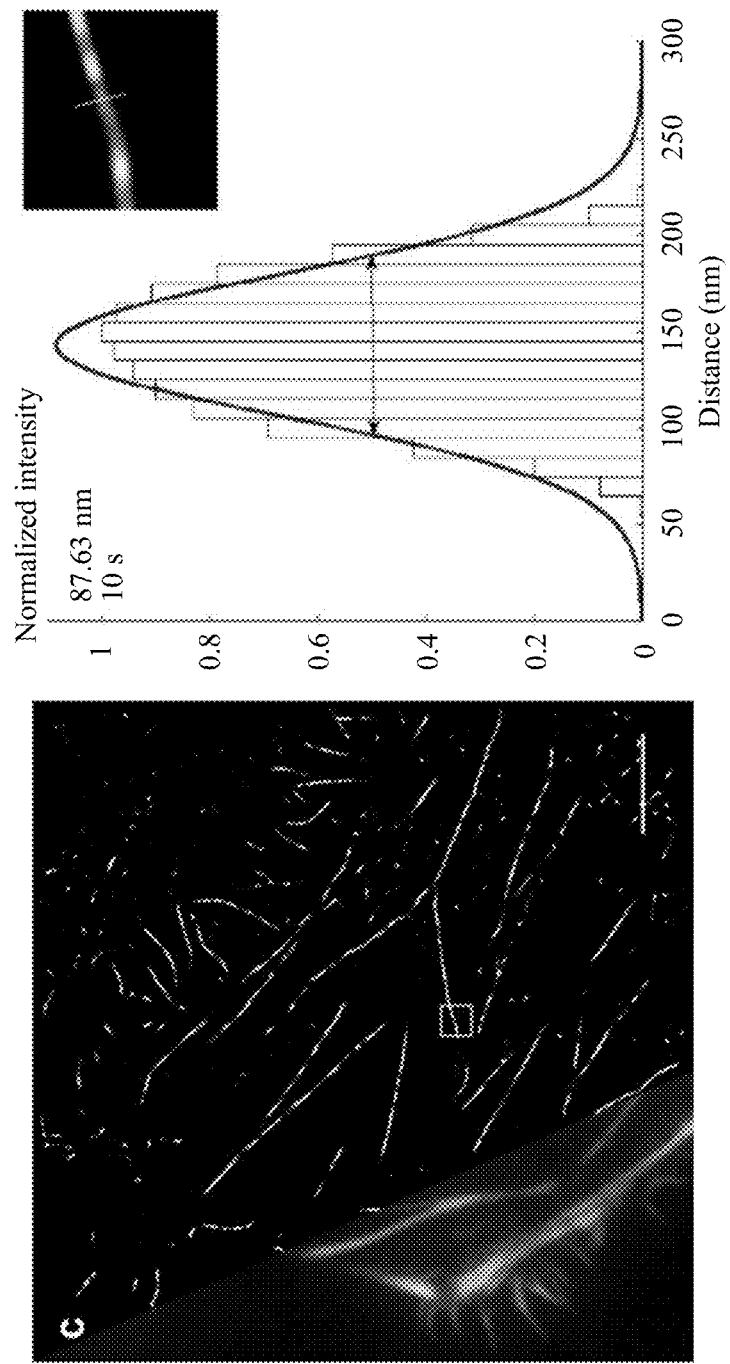

Imaging conditions: a super-resolution microscope N-STORM (Nikon, Japan) or ELYRA P1 (Zeiss, German) was employed. The maximum excitation wavelength of Alexa Fluor 647 was 650 nm and the maximum emission wavelength was 665 nm. The maximum excitation wavelength of Cy3B was 559 nm and the maximum emission wavelength was 570 nm. The maximum excitation wavelength of Atto 488 was 501 nm and the maximum emission wavelength was 523 nm. The laser power was determined according to the method in Example 5. The image was processed by using a low-density localization reconstruction algorithm according to the blinking degree of the sample to obtain a stochastic optical reconstruction super-resolution image (FIGS. 11A-11C). FIGS. 11A-11C showed that compared with the total internal reflection graph prior to calculation (left bottom), the resolution of the stochastic optical reconstruction image (top right) was effectively improved. The resolution imaged with Alexa 647, Cy3B, and Atto 488 can achieve 60 nm (FIG. 11A), 90 nm (FIG. 11B), and 90 nm (FIG. 11C), respectively. The main reason why the spatial resolutions of the dyes were different was that the number of photons emitted by the dyes in each blinking event was different. The number of photons affected the localization accuracy of the algorithm for dye molecules and was a direct factor affecting the spatial resolution. The "bright-dark state" ratio of blinking dyes affected the image quality. This experiment demonstrated the excellent properties of commercial dyes in stochastic optical reconstruction super-resolution image of living cells (excellent blinking ability and high brightness, mainly reflected in the contribution to image quality and spatial resolution), also showed the importance of introducing commercial dyes to fluorescent cell-permeable probes.

Figures 12A, 12B, 12C:
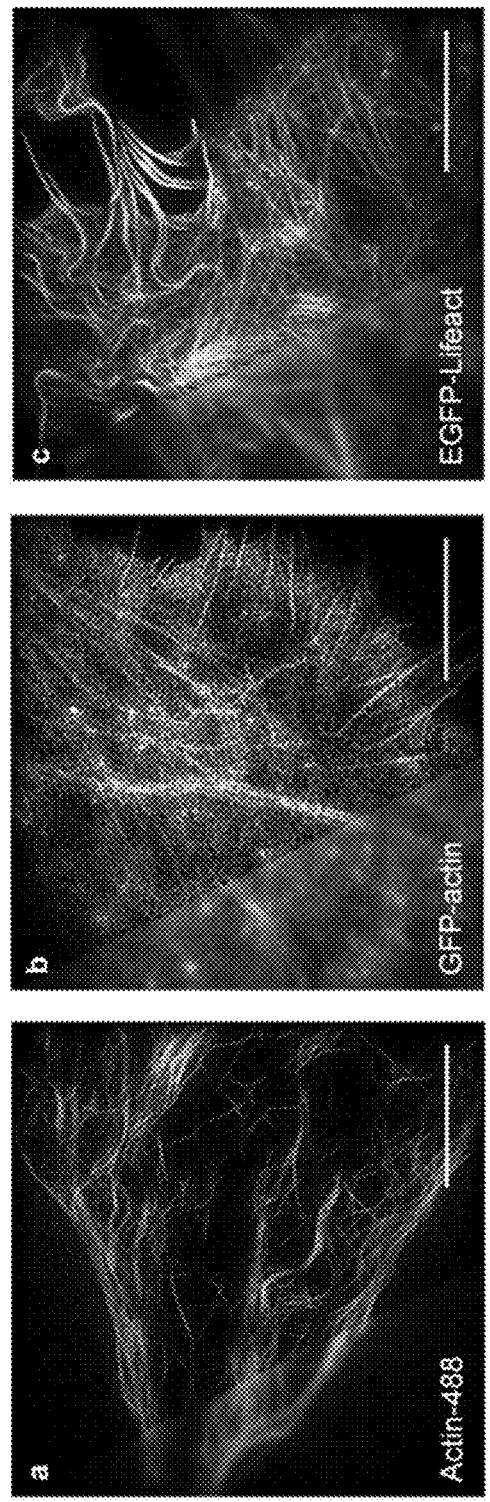
FIGS. 12A-12C show super-resolution imaging by structural illumination microscopy of an actin fluorescent probe based on Atto 488 and standard markers GFP-actin and EGFP-Lifeact, where.

Super-resolution imaging by total internal reflection structural illumination microscopy: a total internal reflection structural illumination microscope (high numerical aperture of 1.78) High-NA TIRF-SIM was employed. The maximum excitation wavelength of Atto 488 was 501 nm and the maximum emission wavelength was 523 nm; the maximum excitation wavelength of EGFP and GFP was 488 nm and the maximum emission wavelength was 507 nm. A sample was imaged using a TIRF-SIM mode, one SIM result was calculated by 9 original images (three angles, three phases), and an exposure time of each original image was 7 ms, as shown in FIGS. 12A-12C. In FIG. 12A, based on the labeling results of the Atto 488 actin fluorescent probe, the intracellular background was very low, and the signal was bright enough, so the signal background ratio was very high and the image was very clear. The fine filament fibers inside the cell or the coarse fibers outside the cell were obvious and clear, especially the coarse fibers which were not clearly distinguished in the TIRF overlay image, a plurality of intertwined bundles of fine fibers were shown in SIM reconstructed images, which proved that SIM imaging can effectively improve the resolution. In FIG. 12B, GFP-actin-labeled filaments had poor signal-to-background ratio, and the background inside cells was high except for coarse fibers. Radial fibers can be seen in filopodia outside the cells. In FIG. 12C, EGFP-Lifeact had a strong signal-to-background ratio. Although the intracellular background was very high, high-quality images can still be obtained. In conclusion, this experiment demonstrated that the actin fluorescent probe based on Atto 488 performed best in super-resolution imaging by structural illumination microscopy because of its excellent brightness, low background (the concentration of probe-incubating cells was controllable) and high resolution.

It will be obvious to those skilled in the art that changes and modifications may be made, and therefore, the aim in the appended claims is to cover all such changes and modifications.

What is claimed is:

1. A peptide, comprising:
   a first fragment comprising $(KG)_n$ or $(GK)_n$ where n is an integer between 2 and 5, K represents lysine, and G represents glycine;
   a second fragment comprising a recognition unit of cysteine protease C1, or a recognition unit of actin; and
   a first connection peptide comprising one or two glycines and being disposed between the first fragment and the second fragment.

2. The peptide of claim 1, wherein n is 3.

3. The peptide of claim 1, further comprising a cell-permeable peptide fragment connected to the first fragment or the second fragment via a second connection peptide.

4. The peptide of claim 3, wherein the cell-permeable peptide fragment has a sequence of rRrRrRRR (SEQ ID NO: 1), where R represents D-arginine, and r represents L-arginine.

5. The peptide of claim 3, wherein the second connection peptide comprises one or two glycines.

6. A fluorescent probe, comprising the peptide of claim 1, wherein lysine of the peptide is coupled to a fluorescent dye.

7. The fluorescent probe of claim 6, wherein the fluorescent dye comprises an N-hydroxysuccinimide (NHS) active group.

8. The fluorescent probe of claim 7, wherein the fluorescent dye is selected from Alexa Fluor 647 NHS ester, Cy3B NHS ester, Atto 565 NHS ester and/or Atto 488 NHS ester.

9. A method of preparing the fluorescent probe of claim 6, comprising:
   1) synthesizing the peptide by using solid phase synthesis, the peptide being coupled to a resin;
   2) separating the peptide from the resin, removing a protective group of a side chain of the peptide, and purifying and concentrating the peptide; and
   3) covalently connecting free amino groups of lysine of the peptide obtained in 2) to an NHS active group of the fluorescent dye by using liquid phase reaction to obtain the fluorescent probe.

10. The method of claim 9, further comprising dissolving the fluorescent probe obtained in 3), and purifying the fluorescent probe by reversed-phase chromatography.

11. The peptide of claim 1, wherein the recognition unit of cysteine protease C1 has a formula of:

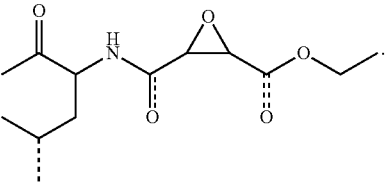

12. The peptide of claim 1, wherein the recognition unit of actin is MGVADLIKKFESISKEE (SEQ ID NO: 2).

13. A peptide, comprising:
   a first peptide fragment comprising $(KG)_n$ or $(GK)_n$, wherein n is an integer between 2 and 5, K represents lysine, and G represents glycine;
   a second peptide fragment comprising a recognition unit of actin; and
   a first connection peptide comprising one or two glycines and being disposed between the first peptide fragment and the second peptide fragment.

14. The peptide of claim 13, wherein n is 3.

15. The peptide of claim 13, wherein the recognition unit of actin is MGVADLIKKFESISKEE (SEQ ID NO: 2).

16. The peptide of claim 13, wherein the peptide further comprises a cell-permeable peptide fragment connected to the first peptide fragment or the second peptide fragment via a second connection peptide.

17. The peptide of claim 16, wherein the cell-permeable peptide fragment has a sequence of rRrRrRRR (SEQ ID NO: 1), where R represents D-arginine, and r represents L-arginine.

18. The peptide of claim 16, wherein the second connection peptide comprises one or two glycines.

19. A fluorescent probe, comprising the peptide of claim 13, wherein lysine of the peptide is coupled to a fluorescent dye.

20. The fluorescent probe of claim 19, wherein the fluorescent dye comprises an N-hydroxysuccinimide (NHS) active group.

* * * * *

SEQUENCE LISTING

```
<160> NUMBER OF SEQ ID NOS: 3

<210> SEQ ID NO 1
<211> LENGTH: 8
<212> TYPE: PRT
<213> ORGANISM: Artificial Sequence
<220> FEATURE:
<223> OTHER INFORMATION: Fully synthetic

<400> SEQUENCE: 1

Arg Arg Arg Arg Arg Arg Arg Arg
1               5

<210> SEQ ID NO 2
<211> LENGTH: 17
<212> TYPE: PRT
<213> ORGANISM: Artificial Sequence
<220> FEATURE:
```

```
<223> OTHER INFORMATION: Fully synthetic

<400> SEQUENCE: 2

Met Gly Val Ala Asp Leu Ile Lys Lys Phe Glu Ser Ile Ser Lys Glu
1               5                   10                  15

Glu

<210> SEQ ID NO 3
<211> LENGTH: 32
<212> TYPE: PRT
<213> ORGANISM: Artificial Sequence
<220> FEATURE:
<223> OTHER INFORMATION: Fully synthetic

<400> SEQUENCE: 3

Met Gly Val Ala Asp Leu Ile Lys Lys Phe Glu Ser Ile Ser Lys Glu
1               5                   10                  15

Glu Gly Lys Gly Lys Gly Lys Gly Arg Arg Arg Arg Arg Arg Arg Arg
                20                  25                  30
```